US011286233B2

(12) United States Patent
Warner

(10) Patent No.: US 11,286,233 B2
(45) Date of Patent: Mar. 29, 2022

(54) STILBENE DERIVATIVES FOR THE TREATMENT OF CNS AND OTHER DISORDERS

(71) Applicant: AMBIENT PHOTONICS, INC., Mill Valley, CA (US)

(72) Inventor: John C. Warner, Wilmington, MA (US)

(73) Assignee: AMBIENT PHOTONICS, INC., Mill Valley, CA (US)

( * ) Notice: Subject to any disclaimer, the term of this patent is extended or adjusted under 35 U.S.C. 154(b) by 51 days.

(21) Appl. No.: 16/611,945

(22) PCT Filed: May 8, 2018

(86) PCT No.: PCT/US2018/031485
§ 371 (c)(1),
(2) Date: Nov. 8, 2019

(87) PCT Pub. No.: WO2018/208709
PCT Pub. Date: Nov. 15, 2018

(65) Prior Publication Data
US 2021/0114976 A1  Apr. 22, 2021

Related U.S. Application Data

(60) Provisional application No. 62/503,654, filed on May 9, 2017.

(51) Int. Cl.
| A61K 31/341 | (2006.01) |
| C07C 255/43 | (2006.01) |
| C07D 209/86 | (2006.01) |
| C07D 215/54 | (2006.01) |

(52) U.S. Cl.
CPC .......... *C07C 255/43* (2013.01); *A61K 31/341* (2013.01); *C07D 209/86* (2013.01); *C07D 215/54* (2013.01)

(58) Field of Classification Search
None
See application file for complete search history.

(56) References Cited

U.S. PATENT DOCUMENTS

| 4,918,215 | A | 4/1990 | Reineht et al. |
| 5,729,322 | A | 3/1998 | Collins et al. |
| 9,421,210 | B2 | 8/2016 | Scott et al. |
| 2009/0211639 | A1* | 8/2009 | Park ..................... H01G 9/2072 136/262 |
| 2012/0302603 | A1 | 11/2012 | Yang et al. |
| 2013/0253064 | A1 | 9/2013 | Scott et al. |
| 2015/0118163 | A1 | 4/2015 | Bhagat et al. |
| 2015/0166495 | A1 | 6/2015 | Scott et al. |

FOREIGN PATENT DOCUMENTS

| CN | 104649949 A | | 5/2015 | |
| JP | WO 2004063283 | * | 7/2004 | ............... C07F 9/38 |

OTHER PUBLICATIONS

International Preliminary Report on Patentability for PCT Patent App. No. PCT/US2018/031485 (dated Nov. 21, 2019).
Yu, X., et al., "Influence of different electron acceptors in organic sensitizers on the performance of dye-sensitized solar cells," Dye and Pigments 2014;102:126-132.
Christoforou, D., et al., "The Application of the Hammett Equation to 13C N.M.R. Spectrometry. VI* Remote Ring Effects in Azobenzenes and Stilbenes," Aust. J. Chem. 1983;36:2083-2094.
Lee, J., et al., "Carbazole-Functionalized Organic Photosensitizer for Dye-Sensitized Solar Cells," J. Nanosci. Nanotech. 2015;15:1434-1442.
Teng, C., et al., "Tuning the HOMO Energy Levels of Organic Dyes for Dye-Sensitized Solar Cells Based on Br-/Br3-Electrolytes," Chem. Eur. J. 2010;16:13127-13138.
Extended European Search Report for European Patent App. No. 18798060.2 (dated Jan. 15, 2021).
International Search Report and Written Opinion for PCT Patent App. No. PCT/US2018/031485.

* cited by examiner

*Primary Examiner* — Samantha L Shterengarts
(74) *Attorney, Agent, or Firm* — Cermak Nakajima & McGwan LLP; Malcolm K. McGowan

(57) ABSTRACT

The present application discloses stilbene derivative compounds and compositions, and methods for treating ocular diseases, neurological disorders and protein aggregation-related disorders in patients using the compounds and compositions as disclosed herein.

8 Claims, No Drawings

STILBENE DERIVATIVES FOR THE TREATMENT OF CNS AND OTHER DISORDERS

TECHNICAL FIELD

Described herein are compounds, compositions and methods for treatment of ocular diseases, neurological disorders and diseases, and protein aggregation-related diseases.

BACKGROUND

Presently, there are no known prevention or cure for neurodegenerative diseases or disorders such as Alzheimer's disease (AD), Parkinson's disease (PD) and prion diseases (PrDs). It has been demonstrated that an aberrant protein has a propensity to aggregate under certain circumstances. The present application discloses compounds, compositions and methods for the treatment of such diseases or disorders.

SUMMARY

Described herein are compounds, compositions and methods for treatment of ocular diseases, neurological disorders and diseases, and protein aggregation-related diseases.

Accordingly, described herein is a compound of formula I:

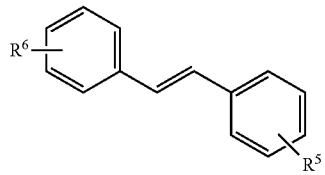
(I)

wherein $R^6$ is selected from the group consisting of —$NR^3R^4$, —$R^3$, —$OR^3$ and halo; $R^5$ is —(CR=CR—)$_n$(CR=$CR^2$—)$R^1$; n is an integer from 0 to 10, $R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, provided that if n=0, and $R^3$ and $R^4$ are both: (a) H; (b) substituted or unsubstituted linear or branched $C_1$-$C_{10}$ alkyl; or (c) substituted or unsubstituted phenyl or $C_6$-$C_{10}$ aryl, then $R^1$ and $R^2$ are not both selected from the group consisting of —H, —CN, —COOR, and —CONHR.

Also described herein is a pharmaceutical composition comprising a therapeutically effective amount of a compound of formula I as described above, and a pharmaceutically acceptable excipient.

Further described herein is a method of treating an ocular disease in a patient in need thereof comprising administering to the patient a therapeutically effective amount of the compound of formula I:

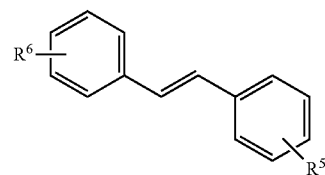
(I)

wherein $R^6$ is selected from the group consisting of —$NR^3R^4$, —$R^3$, —$OR^3$ and halo; $R^5$ is —(CR=CR—)$_n$(CR=$CR^2$—)$R^1$; n is an integer from 0 to 10, $R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, or the compound

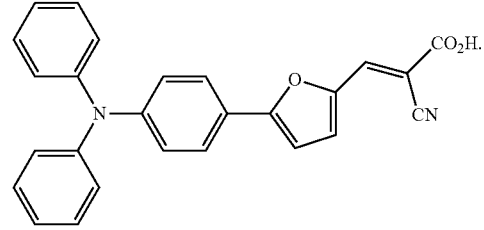 [SMILES: N#C/C(=C\c1ccc(-c2ccc(N(c3ccccc3)c3ccccc3)cc2)o1)C(=O)O]

The ocular disease may be selected from the group consisting of macular degeneration, retinitis pigmentosa, retinopathy, glaucoma and cataracts.

Still further described herein is a method for treating a neurological disorder or disease in a patient in need thereof comprising administering to the patient a therapeutically effect amount of the compound formula I:

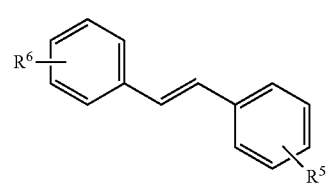
(I)

wherein $R^6$ is selected from the group consisting of —$NR^3R^4$, —$R^3$, —$OR^3$ and halo; $R^5$ is —(CR=CR—)$_n$(CR=$CR^2$—)$R^1$; n is an integer from 0 to 10, $R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, or the compound

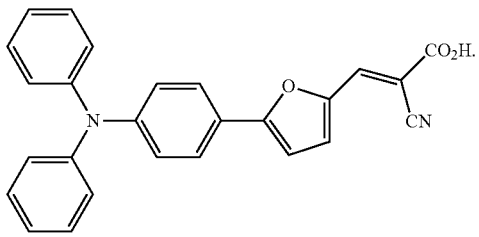 [SMILES: N#C/C(=C\c1ccc(-c2ccc(N(c3ccccc3)c3ccccc3)cc2)o1)C(=O)O]

The neurological disorder or disease may be a neurodegenerative, neurodevelopmental or neuropsychiatric disorder and further may be selected from the group consisting of Alzheimer's disease (AD), amyotrophic lateral sclerosis (ALS), motor neuron disease, Parkinson's disease, Huntington's Disease, prion disease, AIDS or HIV related dementia, cerebral ischemia, cerebrovascular disease, cerebral hemorrhage, Down syndrome, epilepsy, traumatic brain injury, chronic traumatic encephalopathy, traumatic spinal injury, Friedreich's Ataxia, frontotemporal dementia, hemorrhagic stroke, neurodegeneration with Brain Iron Accumulation, Lewy Body Disease, ischemic stroke, multiple sclerosis, Pick's Disease, progressive supranuclear palsy, senile dementia, mild cognitive impairment, hereditary cerebral hemorrhage, traumatic ischemia attack, lead encephalopathy, subdural hematoma, radiation brain injury, Niemann-Pick Disease and neuronal ceroid lipofuscinoses (NCLs; Batten disease).

Also described herein is a method for inhibiting or reversing protein aggregation in a patient comprising administering to the patient a therapeutically effective amount of the compound of formula I:

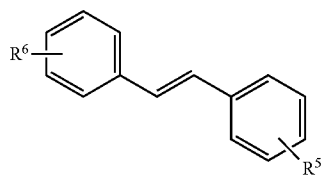

(I)

wherein $R^6$ is selected from the group consisting of —$NR^3R^4$, —$R^3$, —$OR^3$ and halo; $R^5$ is —(CR=CR—)$_n$(CR=$CR^2$—)$R^1$; n is an integer from 0 to 10, $R^1$ and $R^2$ are independently selected from the group consisting of —H, —CN, —COOR, CONHR, CON(H)OR, —$SO_3$R, —$SO_2$R—$OSO_3$R, —$PO_3$HR, and —$OPO_3$HR, further wherein at least one of $R^1$ and $R^2$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, or the compound

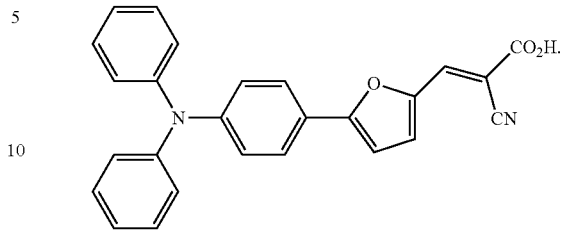

This method is effective to treat a disease selected from the group consisting of type 2 diabetes mellitus, Alzheimer's disease (AD), amyotrophic lateral sclerosis (ALS), motor neuron disease, Parkinson's disease, Huntington's Disease, Creutzfeldt-Jakob disease and prion disease, or alternatively a disease selected from the group consisting of AA amyloidosis, light chain amyloidosis, familial amyloid polyneuropathies, AA (Inflammatory) Amyloidosis, amylin related amyloidosis, familial visceral amyloidosis, primary cutaneous amyloidosis, cerebral amyloid angiopathy, familial corneal amyloidosis and medullary carcinoma of the thyroid.

DETAILED DESCRIPTION

Definitions

Unless specifically noted otherwise herein, the definitions of the terms used are standard definitions used in the art of organic chemistry and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

While particular embodiments are shown and described herein, it will be obvious to those skilled in the art that such embodiments are provided by way of example only. Numerous variations, changes, and substitutions will now occur to those skilled in the art. It should be understood that various alternatives to the embodiments described herein may be employed in practicing the methods described herein. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art. All patents and publications referred to herein are incorporated by reference.

As used in the specification and claims, the singular form "a," "an," and "the" include plural references unless the context clearly dictates otherwise.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

The terms "treatment," "treating," "palliating," and "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

A "pharmaceutically acceptable salt" means a salt composition that is generally considered to have the desired pharmacological activity, is considered to be safe, non-toxic and is acceptable for veterinary and human pharmaceutical applications. Pharmaceutically acceptable salts may be derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions described herein is contemplated. Supplementary active ingredients can also be incorporated into the compositions.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize the limits to the structural nature of the agents described herein.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" as applied to a biologically active agent refers to the agent's ability to selectively reduce the target signaling activity as compared to off-target signaling activity, via direct or interact interaction with the target.

"Subject" refers to an animal, such as a mammal, for example a human. The methods described herein can be useful in both human therapeutics and veterinary applications. In some embodiments, the patient is a mammal, and in some embodiments, the patient is human.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds as described herein wherein one or more hydrogens are replaced by deuterium or tritium, or the replacement of one or more carbon atoms by the $^{13}$C- or $^{14}$C-enriched carbon isotope. Further, substitution with heavier isotopes, particularly deuterium ($^{2}$H or D) may afford certain therapeutic advantages resulting from greater metabolic stability, increased in vivo half-life, reduced dosage requirements or an improvement in therapeutic index. It is understood that deuterium in this context is regarded as a substituent of a compound of the formula (I).

The compounds described herein may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds described herein, whether radioactive or not, are encompassed.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(..+−..)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When the compounds described herein contain olefinic double bonds or other centers of geometric asymmetry, and unless specified otherwise, it is intended that the compounds include both E and Z geometric isomers.

A "substituted" or "optionally substituted" group, means that a group (such as alkyl, aryl, heterocyclyl, cycloalkyl, hetrocyclylalkyl, arylalkyl, heteroaryl, or heteroarylalkyl) unless specifically noted otherwise, may have 1, 2 or 3 —H groups substituted by 1, 2 or 3 substituents selected from halo, trifluoromethyl, trifluoromethoxy, methoxy, —COOH, —CHO, —NH$_2$, —NO$_2$, —OH, —SH, —SMe, —NHCH$_3$, —N(CH$_3$)$_2$, —CN and the like.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization.

A specific example of phenol-keto tautomerization is the interconversion of pyridin-4-ol and pyridin-4(1H)-one tautomers.

Compounds described herein also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound listed above, as well as mixtures thereof, unless a particular crystalline or amorphous form is referred to.

"Solvent," "organic solvent," and "inert solvent" each means a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Compositions

Described herein are compounds of formula I:

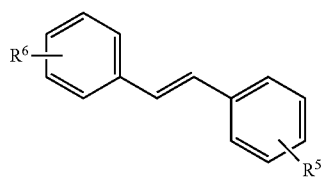

(I)

wherein $R^6$ is selected from the group consisting of —$NR^3R^4$, —$R^3$, —$OR^3$ and halo; $R^5$ is —(CR=CR—)$_n$(CR=CR$^2$—)$R^1$;

n is an integer from 0 to 10;

$R^1$ and $R^2$ are independently selected from the group consisting of —H, —CN, —COOR, CONHR, CON(H)OR, —SO$_3$R, —SO$_2$R—OSO$_3$R, —PO$_3$HR, and —OPO$_3$HR, further wherein at least one of $R^1$ and $R^2$ is not —H;

each R is independently selected from —H and C$_{1-6}$ linear or branched alkyl; and $R^3$ and $R^4$ are independently selected from the group consisting of H, substituted or unsubstituted linear or branched C$_1$-C$_{10}$ alkyl, substituted or unsubstituted phenyl, substituted or unsubstituted C$_6$-C$_{10}$ aryl, substituted or unsubstituted C$_5$-C$_1$ heteroaryl, substituted or unsubstituted C$_5$-C$_{10}$ cycloalkyl, and substituted or unsubstituted C$_5$-C$_{10}$ heterocycloalkyl; or N, $R^3$ and $R^4$ together form a ring that is substituted or unsubstituted C$_5$-C$_{10}$ heterocycloalkyl, provided that if n=0, and $R^3$ and $R^4$ are both: (a) H; (b) substituted or unsubstituted linear or branched C$_1$-C$_{10}$ alkyl; or (c) substituted or unsubstituted phenyl or C$_6$-C$_{10}$ aryl, then $R^1$ and $R^2$ are not both selected from the group consisting of —H, —CN, —COOR, and —CONHR.

In preferred embodiments, the compound may be of formula II, III or IV:

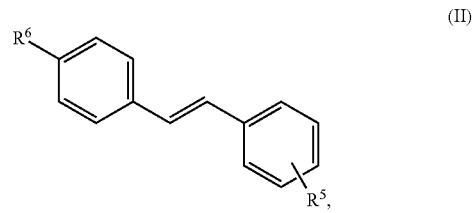

(II)

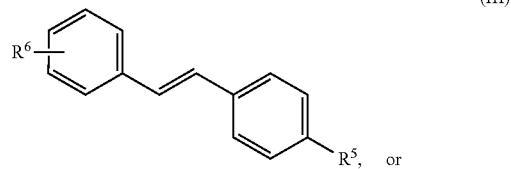

(III)

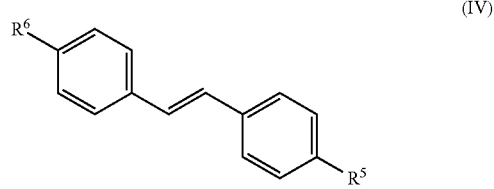

(IV)

where $R^5$ and $R^6$ are as described in the preceding paragraph.

The structures of the compounds described herein, as shown in formulae I-IV, have a central stilbene structure with two substituent moieties, $R^5$ and $R^6$, attached thereto. One substituent moiety is attached to any position on each of the phenyl moieties, as shown in formula I. In preferred embodiments, the substituent moieties are attached to preferred positions on the phenyl moieties as shown in formulae II-IV.

In general, the substituent moiety $R^6$ will be a pi electron-donating moiety, and the other substituent moiety $R^5$ will be a pi electron-withdrawing moiety. The pi electron-donating moiety is preferably an amino, alkyl or alkoxy moiety represented herein by —$NR^3R^4$, —$R^3$, or —$OR^3$. A particularly preferred pi electron-donating moiety is the amino moiety —$NR^3R^4$, and in an even more preferred embodiment is selected from the group consisting of diethylamino, diphenylamino, methyl(phenyl)amino, cyclohexyl(methyl)amino, bis(4-methoxyphenyl)amino, bis(4-(tert-butyl)phenyl)amino, di(pyridin-2-yl)amino, di(pyridin-3-yl)amino, di(pyridin-4-yl)amino, piperidin-1-yl, 4-methylpiperazin-1-yl, 4-phenylpiperazin-1-yl, pyrrolidin-1-yl, and morpholino. In other preferred embodiments, the pi electron-donating moiety is —$R^3$, or —$OR^3$, and preferably selected from the group consisting of 3',4'-dimethoxyphenyl, tert-butyl, phenyoxy, and methoxy. In still another preferred embodiment, the pi electron-donating moiety is halo selected from fluoro, bromo, chloro, and iodo, most preferably bromo.

The pi electron-withdrawing moiety $R^5$ may be —H, —CN, —COOR, CONHR, CON(H)OR, —SO$_3$R, —SO$_2$R—OSO$_3$R, —PO$_3$HR, or —OPO$_3$HR, and maybe directly attached to the central structure, or linked via from one to about ten conjugated carbon-carbon double bonds. This moiety is represented herein by the structure —(CR=CR—)$_n$(CR=CR$^2$—)$R^1$, wherein n is an integer from 0 to 10; and $R^1$ and $R^2$ are independently selected from the group consisting of —H, —CN, —COOR, CONHR, CON(H)OR, —SO$_3$R, —SO$_2$R—OSO$_3$R, —PO$_3$HR, or —OPO$_3$HR, further wherein at least one of $R^1$ and $R^2$ is not —H. As used herein, each R is independently selected from —H and $C_{1-6}$ linear or branched alkyl. In a particular preferred embodiment, $R^1$ and $R^2$ together are —CN and —COOH, n=0 and m=1.

In the compounds described herein, $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or N, $R^3$ and $R^4$ together form a ring that is substituted or unsubstituted $C_5$-$C_{10}$ heterocycloalkyl. In particularly preferred embodiments, $R^3$ and $R^4$ are methyl, ethyl, cyclohexyl, phenyl, 4-methoxyphenyl, 4-(tert-butyl)phenyl, pyridin-2-yl, pyridin-3-yl, or pyridin-4-yl, or N, $R^3$ and $R^4$ together are piperidin-1-yl, 4-methylpiperazin-1-yl, 4-phenylpiperazin-1-yl, pyrrolidin-1-yl, or morpholino.

The following preferred compounds of the invention have been synthesized:

| Entry | Structure | Compound # |
|---|---|---|
| 1 | 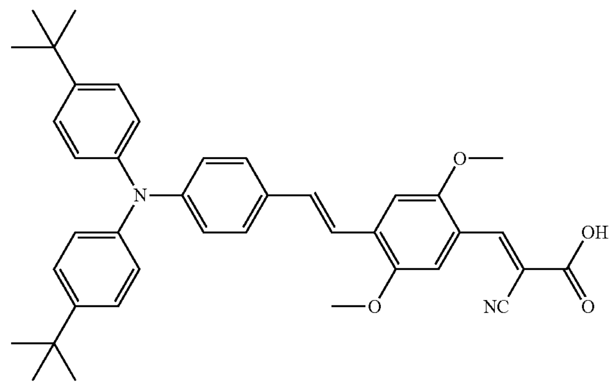 [SMILES: COc1cc(/C=C(\C#N)C(=O)O)c(OC)cc1/C=C/c1ccc(N(c2ccc(C(C)(C)C)cc2)c2ccc(C(C)(C)C)cc2)cc1] | WBI-PC-63 |
| 2 | 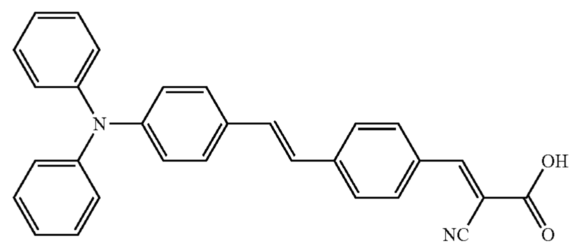 [SMILES: N#C/C(=C\c1ccc(/C=C/c2ccc(N(c3ccccc3)c3ccccc3)cc2)cc1)C(=O)O] | WBI-PC-64 |
| 3 | 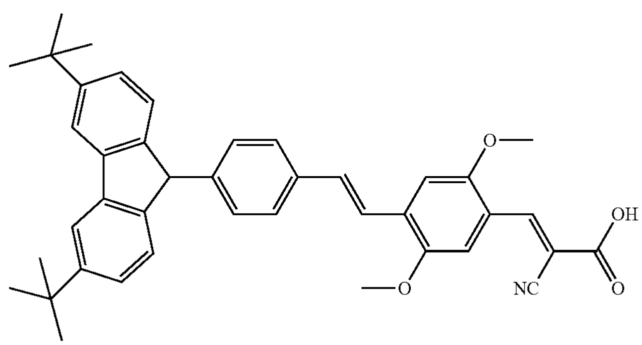 [SMILES: COc1cc(/C=C(\C#N)C(=O)O)c(OC)cc1/C=C/c1ccc(C2c3ccc(C(C)(C)C)cc3-c3cc(C(C)(C)C)ccc32)cc1] | WBI-PC-66 |
| 4 | 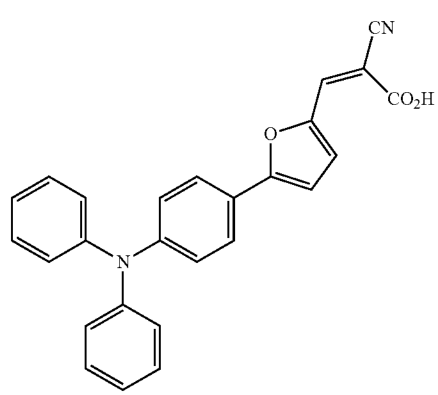 [SMILES: N#C/C(=C/c1ccc(-c2ccc(N(c3ccccc3)c3ccccc3)cc2)o1)C(=O)O] | WBI-PC-81 |

-continued
| Entry | Structure | Compound # |
|---|---|---|
| 5 | 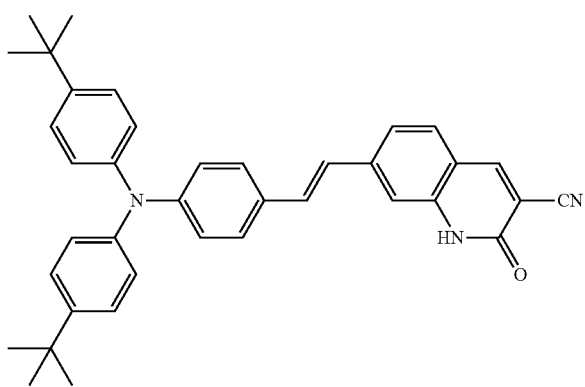 [SMILES: CC(C)(C)c1ccc(N(c2ccc(/C=C/c3ccc4cc(C#N)c(=O)[nH]c4c3)cc2)c2ccc(C(C)(C)C)cc2)cc1] | WBI-PC-174 |
| 6 | 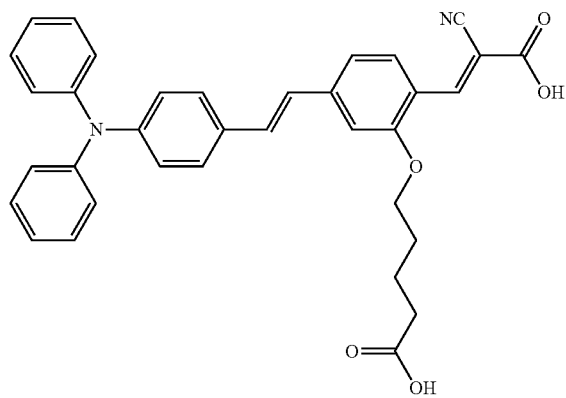 [SMILES: N#C/C(=C\c1ccc(/C=C/c2ccc(N(c3ccccc3)c3ccccc3)cc2)cc1OCCCCC(=O)O)C(=O)O] | WBI-PC-78 |
| 7 | 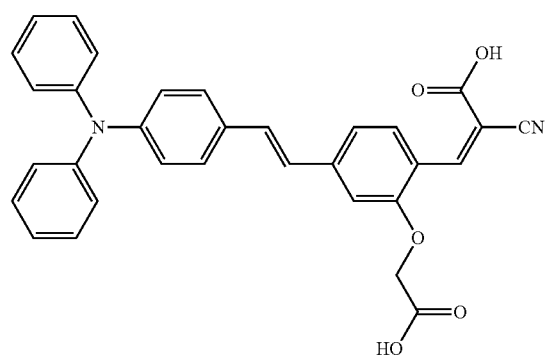 [SMILES: N#C/C(=C/c1ccc(/C=C/c2ccc(N(c3ccccc3)c3ccccc3)cc2)cc1OCC(=O)O)C(=O)O] | WBI-PC-190 |

-continued

| Entry | Structure | Compound # |
|---|---|---|
| 8 | 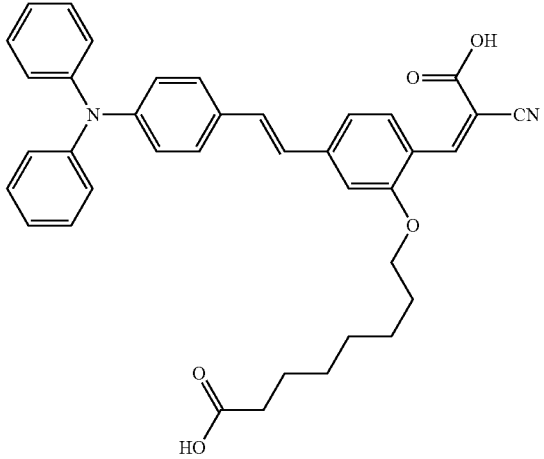 Target 2 | WBI-PC-191 |
| 9 | 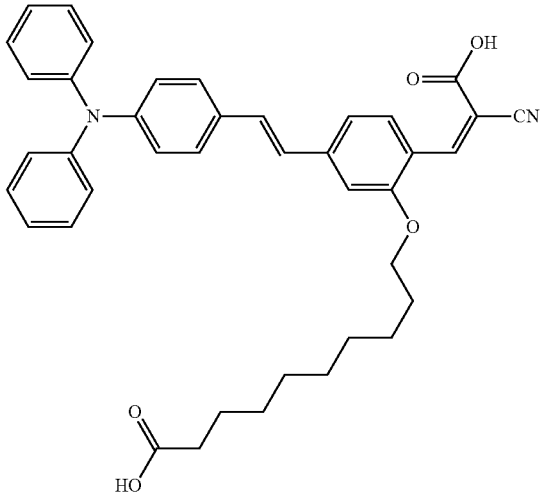 Target 3 | WBI-PC-192 |

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein. However, other equivalent separation or isolation procedures can also be used.

When desired, the (R)- and (S)-isomers of the compounds described herein, if present, may be resolved by methods known to those skilled in the art, for example by formation of diastereomeric salts or complexes which may be separated, for example, by crystallization; via formation of diastereomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes or derivatives, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") include those embodiments, for example, an embodiment of any composition of matter, composition, method, or process, or the like, that "consist of" or "consist essentially of" the described features.

The subject pharmaceutical compositions are typically formulated to provide a therapeutically effective amount of a compound of Formula I as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, a compound of Formula I and other agent(s) may be mixed into a preparation or both components may be formulated into separate preparations to use them in combination separately or at the same time. A compound as described herein may also be used in combination with other agents, e.g., an additional disaggregating agent that is or is not of Formula I, for treatment of a the diseases listed herein in a subject. Suitable agents for use in combination with the compounds described herein, including compounds of Formula (I) and subgenera thereof, include compounds of the formula:

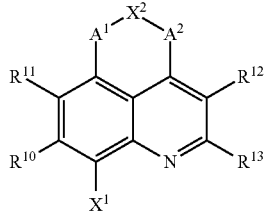

I wherein: $X^1$ is —$OR^1$ or —$NR^1R^2$; $X^2$ is selected from the group consisting of —$NR^3$—, —O— and —$S(O)_{1-2}$—; $A^1$ is selected from the group consisting of —$C(R^4R^5)$—, —C(O)—, —C(S)— and —$C(NR^6)$—; $A^2$ is selected from the group consisting of —$C(R^7R^8)$—, —C(O)—, —C(S)— and —$C(NR^9)$—; $R^1$ and $R^2$ are each independently H, substituted or unsubstituted $C_{1-6}$ alkyl, X—$C_{1-6}$ alkyl, substituted or unsubstituted $C_{5-10}$ aryl, substituted or unsubstituted —$C_{1-6}$ alkyl-$C_{6-10}$ aryl, substituted or unsubstituted $C_{1-6}$ alkyC(O)—, X—$C_{1-6}$ alkyC(O)—, substituted or unsubstituted $C_{1-6}$ alkylS(O)$_{1-2}$—, substituted or unsubstituted $C_{1-6}$ alkylNR'C(O)—, X—$C_{1-6}$ alkylNR'C(O)—, X—$C_{1-6}$ alkoxyC(NR")— and substituted or unsubstituted $C_{1-6}$ alkoxyC(NR")—; R' and R" are each independently selected from the group consisting of H, substituted or unsubstituted $C_{1-6}$ alkyl and substituted and unsubstituted —$C_{1-6}$ alkyl-$C_{6-10}$ aryl; $R^3$ is H or selected from the group consisting of substituted or unsubstituted $C_{1-6}$ alkyl, substituted or unsubstituted $C_{5-10}$ aryl, substituted or unsubstituted —$C_{1-6}$ alkyl-$C_{6-10}$ aryl, substituted or unsubstituted —$C_{1-6}$ alkyl-$C_{5-10}$ heteroaryl, substituted or unsubstituted $C_{1-6}$ alkylC(O)—, substituted or unsubstituted $C_{1-6}$ alkyl-S(O)$_{1-2}$—, substituted or unsubstituted $C_{1-6}$ alkylNHC(O)— and substituted or unsubstituted $C_{1-6}$ alkoxyC(NR')—; $R^4$, R, $R^6$, $R^7$, $R^8$ and $R^9$ are each independently H or selected from the group consisting of substituted or unsubstituted $C_{1-6}$ alkyl, substituted or unsubstituted $C_{1-6}$ alkylC(O)—, substituted or unsubstituted $C_{1-6}$ alkoxyC(O)—, substituted or unsubstituted —$C_{1-6}$ alkyl-$C_{6-10}$ aryl and substituted or unsubstituted $C_{5-10}$ aryl; $R^{10}$, $R^{11}$ and $R^{12}$ are each independently H or selected from the group consisting of substituted or unsubstituted $C_{1-6}$ alkyl, X—$C_{1-6}$alkyl, X—$C_{1-6}$ alkylC(O)— and substituted or unsubstituted $C_{1-6}$ alkylC(O)—; $R^{13}$ is H or is selected from the group consisting of X, halo, —OR', —CN, —SR', —NR'R", —$NO_2$, —$CO_2R'$, —$SO_3R'$, substituted or unsubstituted $C_{1-6}$ alkyl, $C_{1-6}$ alkyl-X, —$C_{1-6}$ alkyl-SH, substituted or unsubstituted $C_{1-6}$ alkoxy-, substituted or unsubstituted $C_{1-6}$ alkylC(O)—, X—$C_{1-6}$ alkylC(O)—, substituted or unsubstituted $C_{1-6}$ alkylC(S)—, X—$C_{1-6}$ alkyl C(S)—, —$(CH_2)_n$—NH—$(CH_2)_m$—NR'R", $C_{1-6}$ alkylC(NR')—, X—$C_{1-6}$ alkylC(NR')—, X—$C_{1-6}$ alkylC(NOH)—, $C_{1-6}$ alkylC(NOH)—, —$(CH_2)_n$—C(NOH)—$C_{1-6}$ alkyl, $C_{5-10}$ aryl, —$C_{1-6}$ alkyl-$C_{6-10}$ aryl, —$C_{1-6}$ alkyl-$C_{3-10}$ heteroaryl, and —$C_{3-10}$ heteroaryl; each X is independently selected from the group consisting of $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O and $^{76}$Br; and m and n are each independently 1, 2 or 3. Suitable compounds of this formula are described in WO2014/052906.

In some embodiments, the concentration of one or more of the compounds of Formula I in the pharmaceutical compositions described herein is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of Formula I is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of Formula I is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more of the compounds of Formula I is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of Formula I is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of Formula I is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of Formula I is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds of Formula I described herein are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound of Formula I is administered, the subject to be treated, the body weight of the subject to be treated, and the preference and experience of the attending physician.

A pharmaceutical composition described herein typically contains an active ingredient (e.g., a compound of Formula I or a pharmaceutically acceptable salt and/or coordination complex thereof), and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration

Described herein is a pharmaceutical composition for oral administration containing a compound of Formula I:

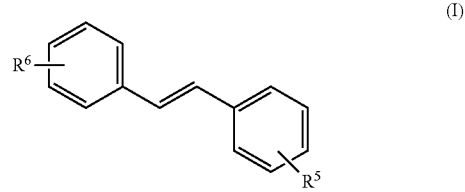

(I)

wherein $R^6$ is selected from the group consisting of $-NR^3R^4$, $-R^3$, $-OR^3$ and halo; $R^5$ is $-(CR=CR-)_n(CR=CR^2-)R^1$; n is an integer from 0 to 10, $R^1$ and $R^2$ are independently selected from the group consisting of $-H$, $-CN$, $-COOR$, $CONHR$, $CON(H)OR$, $-SO_3R$, $-SO_2R-OSO_3R$, $-PO_3HR$, and $-OPO_3HR$, further wherein at least one of $R^1$ and $R^2$ is not $-H$; each R is independently selected from $-H$ and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_1$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, provided that if n=0, and $R^3$ and $R^4$ are both: (a) H; (b) substituted or unsubstituted linear or branched $C_1$-$C_{10}$ alkyl; or (c) substituted or unsubstituted phenyl or $C_6$-$C_{10}$ aryl, then $R^1$ and $R^2$ are not both selected from the group consisting of $-H$, $-CN$, $-COOR$, and $-CONHR$, and a pharmaceutical excipient suitable for oral administration.

Also described herein is a solid pharmaceutical composition for oral administration containing: (i) an effective amount of a compound of Formula I; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

Also described herein are anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. Pharmaceutical compositions and dosage forms which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions described herein to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin, and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound described herein and to minimize precipitation of the compound described herein. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

Described herein are pharmaceutical compositions for injection containing a compound of Formula I:

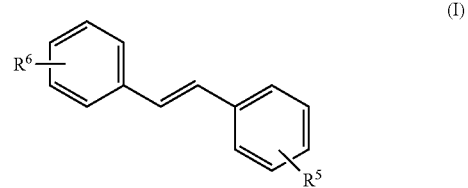

wherein $R^6$ is selected from the group consisting of —$NR^3R^4$, —$R^3$, —$OR^3$ and halo; $R^5$ is —$(CR=CR—)_n$ $(CR=CR^2—)R^1$; n is an integer from 0 to 10, $R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, provided that if n=0, and $R^3$ and $R^4$ are both: (a) H; (b) substituted or unsubstituted linear or branched $C_1$-$C_{10}$ alkyl; or (c) substituted or unsubstituted phenyl or $C_6$-$C_{10}$ aryl, then $R^1$ and $R^2$ are not both selected from the group consisting of —H, —CN, —COOR, and —CONHR, and a pharmaceutical excipient suitable for injection. Components and amounts of agents in the compositions are as described herein.

The forms in which the novel compositions described herein may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

Also described herein is a pharmaceutical composition for transdermal delivery containing a compound of Formula I:

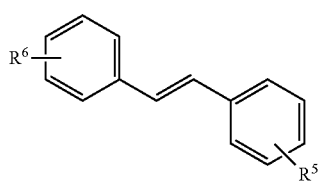

(I)

wherein $R^6$ is selected from the group consisting of —$NR^3R^4$, —$R^3$, —$OR^3$ and halo; $R^5$ is —$(CR{=}CR{-})_n$ $(CR{=}CR^2{-})R^1$; n is an integer from 0 to 10, $R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, provided that if n=0, and $R^3$ and $R^4$ are both: (a) H; (b) substituted or unsubstituted linear or branched $C_1$-$C_{10}$ alkyl; or (c) substituted or unsubstituted phenyl or $C_6$-$C_{10}$ aryl, then $R^1$ and $R^2$ are not both selected from the group consisting of —H, —CN, —COOR, and —CONHR, and a pharmaceutical excipient suitable for transdermal delivery.

Compositions described herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, or dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods described herein employs transdermal delivery devices ("patches"). Such transdermal patches may be used to provide continuous or discontinuous infusion of a compound of Formula I in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on-demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2004; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds of Formula I or pharmaceutical compositions described herein can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of a compound of Formula I administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of Formula I is administered in a single dose. Typically, such administration will be by injection, e.g., intravenous injection, in order to introduce the agent quickly. However, other routes may be used as appropriate.

In some embodiments, a compound of Formula I is administered in multiple doses. Dosing may be about once, twice, three times, four times, five times, six times, or more than six times per day. Dosing may be about once a month, once every two weeks, once a week, or once every other day. In another embodiment a compound and another agent are administered together about once per day to about 6 times per day. In another embodiment the administration of a compound of Formula I and an agent continues for less than about 7 days. In yet another embodiment the administration continues for more than about 6, 10, 14, 28 days, two months, six months, or one year. In some cases, continuous dosing is achieved and maintained as long as necessary.

Administration of the compound(s) of Formula I may continue as long as necessary. In some embodiments, a compound of Formula I is administered for more than 1, 2, 3, 4, 5, 6, 7, 14, or 28 days. In some embodiments, a compound of Formula I is administered for less than 28, 14, 7, 6, 5, 4, 3, 2, or 1 day. In some embodiments, a compound of Formula I is administered chronically on an ongoing basis, e.g., for the treatment of chronic effects.

An effective amount of a compound of Formula I may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions described herein may also be delivered via an impregnated or coated device such as a stent, for example, or an artery-inserted cylindrical polymer. A compound of Formula I may be administered, for example, by local delivery from the struts of a stent, from a stent graft, from grafts, or from the cover or sheath of a stent. In some embodiments, a compound of Formula I is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be non-degrading or may degrade with time, releasing the compound or compounds. A compound of Formula I may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, a compound of Formula I may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of a compound of Formula I in a suitable solvent, followed by evaporation of the solvent. Excess drug on the surface of the stent may be removed via an additional brief solvent wash. In yet other embodiments, a compound of Formula I may be covalently linked to a stent or graft. A covalent linker may be used which degrades in vivo, leading to the release of a compound of Formula I. Any bio-labile linkage may be used for such a purpose, such as ester, amide or anhydride linkages. A compound of Formula I may additionally be administered intravascularly from a balloon used during angioplasty. Extravascular administration of a compound of Formula I via the pericard or via adventitial application of formulations described herein may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of Formula I may be administered in dosages. It is known in the art that due to inter-subject variability in compound pharmacokinetics, individualization of dosing regimen is necessary for optimal therapy. Dosing for a compound of Formula I may be found by routine experimentation in light of the instant disclosure.

When a compound of Formula I, is administered in a composition that comprises one or more agents, and the agent has a shorter half-life than the compound of Formula I unit dose forms of the agent and the compound of Formula I may be adjusted accordingly.

The subject pharmaceutical composition may, for example, be in a form suitable for oral administration as a tablet, capsule, pill, powder, sustained release formulations, solution, or suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound of Formula I as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Kits are also described herein. The kits include one or more compounds of Formula I as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, a compound of Formula I and the agent are provided as separate compositions in separate containers within the kit. In some embodiments, the compound described herein and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Therapeutic Methods

The compounds and pharmaceutical compositions described herein, in therapeutically effective amounts and as described above, are useful in methods to treat ocular diseases, neurological diseases, and protein aggregation-related diseases.

The therapeutic methods described herein comprise the step of administering a therapeutically effective amount of the compound

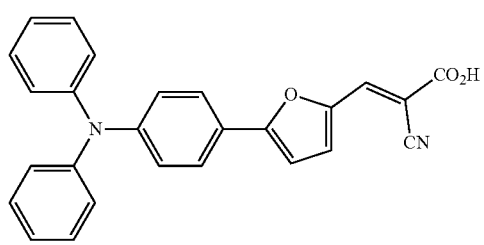 [SMILES: N#C/C(=C\c1ccc(-c2ccc(N(c3ccccc3)c3ccccc3)cc2)o1)C(=O)O]

or a compound of formula I:

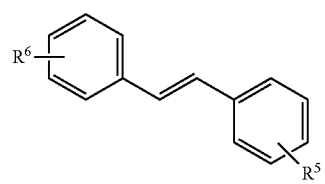

(I)

wherein $R^6$ is selected from the group consisting of —$NR^3R^4$, —$R^3$, —$OR^3$ and halo;
$R^5$ is —(CR=CR—)$_n$(CR=CR$^2$—)$R^1$;
n is an integer from 0 to 10;
$R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H;
each R is independently selected from —H and $C_{1-6}$ linear or branched alkyl; and
$R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or N, $R^3$ and $R^4$ together form a ring that is substituted or unsubstituted $C_5$-$C_{10}$ heterocycloalkyl.

In preferred embodiments, the compound may be of formula II, III or IV:

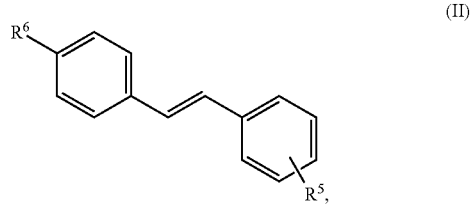

(II)

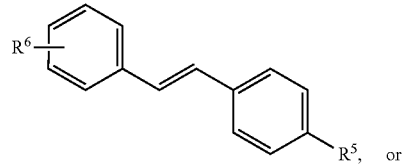

(III)

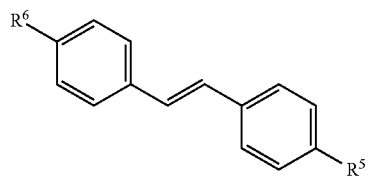

(IV)

where $R^5$ and $R^6$ are as described in the preceding paragraph.

In one embodiment, the therapeutically effective amount of a compound described above is used in methods to treat an ocular disease selected from the group consisting of macular degeneration, retinitis pigmentosa, retinopathy, glaucoma and cataracts.

In another embodiment, the therapeutically effective amount of a compound described above is used in methods to treat a neurological disorder or disease or a neurodegenerative disease.

In one aspect of the above, the neurological disorder or disease is a neurodegenerative, neurodevelopmental or neuropsychiatric disorder. In another aspect of the above method, the neurodegenerative disorder or disease is selected from the group consisting of Alzheimer's disease (AD), amyotrophic lateral sclerosis (ALS), motor neuron disease, Parkinson's disease, Huntington's Disease, prion disease, AIDS or HIV related dementia, cerebral ischemia, cerebrovascular disease, cerebral hemorrhage, Down Syndrome, epilepsy, traumatic brain injury, chronic traumatic encephalopathy, traumatic spinal injury, Friedreich's Ataxia, frontotemporal dementia, hemorrhagic stroke, Neurodegeneration with Brain Iron Accumulation, Lewy Body Disease, ischemic stroke, multiple sclerosis, Pick's Disease, progressive supranuclear palsy, senile dementia, mild cognitive impairment, hereditary cerebral hemorrhage, traumatic ischemia attack, lead encephalopathy, subdural hematoma, radiation brain injury, Niemann-Pick Disease and neuronal ceroid lipofuscinoses (NCLs; Batten disease).

In another embodiment, the therapeutically effective amount of a compound described above is used in methods to inhibit protein aggregation in a patient with a protein aggregation-related disease. In one aspect of the above method, the disease is selected from the group consisting of type 2 diabetes mellitus, Alzheimer's disease (AD), amyotrophic lateral sclerosis (ALS), motor neuron disease, Parkinson's disease, Huntington's Disease, Creutzfeldt-Jacob disease and prion disease. In another aspect, the therapeutically effective amount is effective to treat a disease selected from the group consisting of AA amyloidosis, light chain amyloidosis, familial amyloid polyneuropathies, AA (Inflammatory) Amyloidosis, amylin related amyloidosis, familial visceral amyloidosis, primary cutaneous amyloidosis, cerebral amyloid angiopathy, familial corneal amyloidosis and medullary carcinoma of the thyroid.

EXPERIMENTAL

All reagents were purchased from commercial suppliers and used as supplied unless stated otherwise. Reactions were carried out in air unless stated otherwise. 400 MHz $^1$H NMR spectra were obtained on a JEOL AS 400 spectrometer. Low-resolution mass spectra (LRMS) were obtained on a JEOL JMS-T100LC DART/AccuTOF mass spectrometer. Measurement of reversal of protein aggregation may be carried out using such assays as Bis-ANS Fluorescence as described in, for example, W. T. Chen et al., J. Biol. Chem, 2011, 286 (11), 9646.

General synthetic scheme for making the compounds herein:

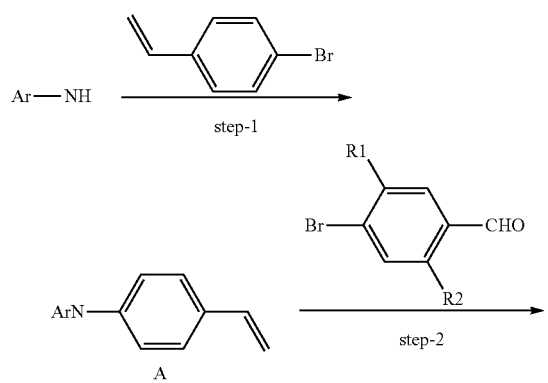

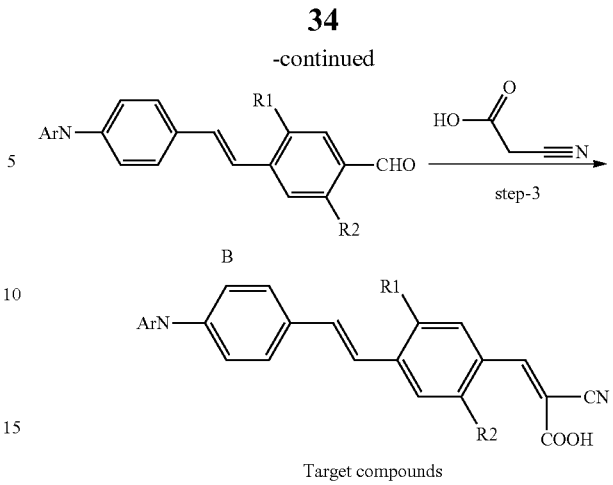

Example 1

Synthesis of (Z)-3-[4-[(E)-2-[4-(4-tert-butyl-N-(4-tert-butylphenyl)anilino)phenyl]vinyl]-2,5-dimethoxy-phenyl]-2-cyano-prop-2-enoic Acid (WBI-PC-63)

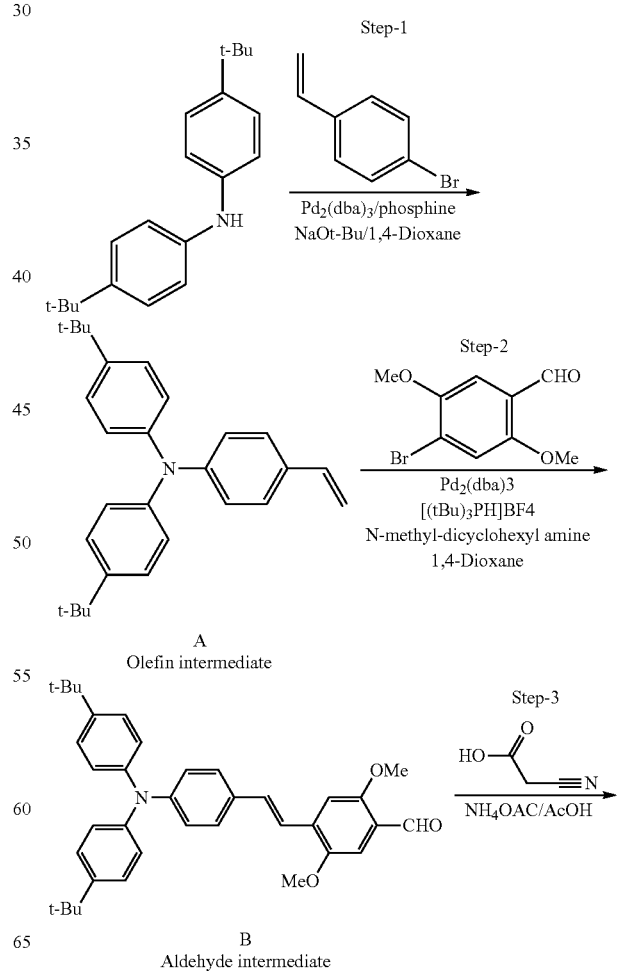

-continued

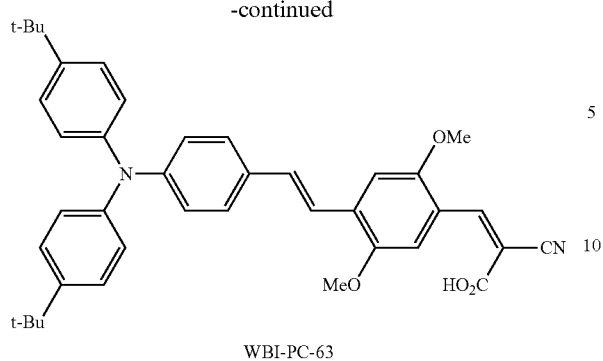

WBI-PC-63

This is the synthetic scheme for Example 1.

Synthesis of Olefin Intermediate A

To a mixture of Bis((4-t-butyl)phenyl)amine (15.0 g, 0.053 mol) and 4-bromostyrene (~7 mL, 0.053 mol, 1 equiv.) in an oven dried 500 mL Schlenck flask was added Pd$_2$(dba)$_3$ (488 mg, 0.533 mmol), phosphine (360 mg, 1.06 mmol) and NaOtBu (5.63 g, 0.059 mol). The flask was flushed with N$_2$ for 10 min, treated with degassed 1,4-dioxane (50 mL) and the mixture was heated to 80° C. for 1.5 hours under N$_2$. The reaction was monitored by TLC for completion before cooling to room temperature. The organic layer was washed with DI water (2×100 mL) and then saturated brine solution (100 mL). The combined organic layer was then dried with anhydrous Na$_2$SO$_4$ and concentrated. The resulting crude olefin was used directly in the following step without further purification.

Synthesis of Aldehyde Intermediate B

To the dark brown olefin (olefin intermediate A) in the Schlenck flask under N$_2$ was added 4-bromo-2,5-dimethoxy benzaldehyde (13.0 g, 0.053 mol), N-methyl-dicylohexyl amine (23 mL, 0.112 mol), Pd$_2$(dba)$_3$ (488 mg, 0.533 mmol), and the phosphine salt (307 mg, 1.06 mmol) under N$_2$. Dry and degassed 1,4-dioxane (25 mL) was then added to the flask and the mixture was stirred at 60° C. under N$_2$ for 2.5 hours. The mixture turned from purple to yellow green during the course of the reaction. Crude LCMS showed the reaction was complete, and the mixture was filtered and the collected solid washed with copious amounts of CH$_2$Cl$_2$ to separate the product from the inorganic materials. The combined CH$_2$Cl$_2$/dioxane layer was concentrated under reduced pressure. The resulting orange-red residue was dissolved in CH$_2$Cl$_2$ (60 mL) and washed with 1N HCl (150 mL). The aqueous layer was extracted with CH$_2$Cl$_2$ (2×25 mL), and the combined organic layer was concentrated under reduced pressure to give a reddish yellow residue, which was dried on the vacuum line for 1 hour at room temperature and the resulting reddish yellow crude solid product was used directly in the following reaction without further purification.

Synthesis of WBI-PC-63

To the aldehyde intermediate B was added glacial acetic acid (150 mL) followed by cyanoacetic acid (11.0 g, 0.129 mol) and ammonium acetate (12.3 g, 0.160 mol), and the reaction was refluxed for 5 hours. The reaction was then cooled to room temperature, and was then slowly added to ice-cold DI water (1.5 L), and stirred at room temperature for 1 hour. The precipitate was filtered and washed with DI water and hexanes, and dried overnight in a vacuum oven at 60° C. to afford WBI-PC-63 as a dark red solid. (31.5 g; 95% overall yield). LCMS (M+1): 615.3; 1H NMR (400 MHz, d6-DMSO): 8.52 (s, 1H), 7.85 (s, 1H), 7.46-6.86 (m, 15H), 3.94 (s, 3H), 3.83 (s, 3H), 1.26 (s, 18H).

Example 2

Synthesis of (Z)-2-cyano-3-[4-[(E)-2-[4-(N-phenylanilino)phenyl]vinyl]phenyl]prop-2-enoic Acid (WBI-PC-64)

Synthetic Scheme:

Scheme-3: Synthesis of WBI-PC-64

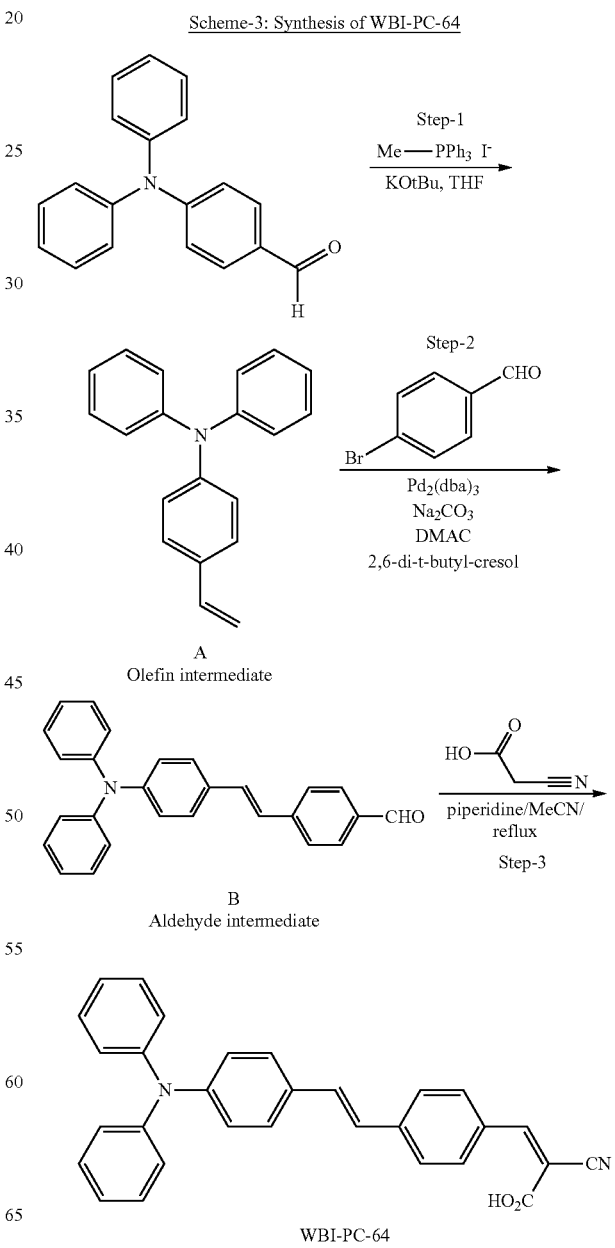

WBI-PC-64

Synthesis of Olefin Intermediate A

The starting aldehyde (4.5 g, 0.0165 mol) was placed in a pear shaped flask with 25 mL of dry THF and the yellow solution was degassed for 20 min with $N_2$. KOtBu (2.5 g, 1.25 equiv.) and methyltriphenylphosphonium iodide (8.33 g, 1.25 equiv.) were combined in a separate 250 mL Schlenck flask equipped with a stirbar and placed under $N_2$. The THF solution of A was then canula transferred under $N_2$ into the Schlenck flask. The solution was stirred at room temperature under $N_2$ for 5 hr. The reaction mixture was partitioned between 125 mL of $CH_2Cl_2$ and 100 mL of DI water. The mixture was acidified using concentrated HCl (pH~4). The separated organic layer was then washed with DI water (2×100 mL) and then saturated brine solution (100 mL). The combined organic layer was then dried over anhydrous $Na_2SO_4$ and concentrated under reduced pressure. 1H NMR of the crude product confirmed the formation of the desired Wittig product. The crude material was then purified on silica gel using n-hexanes as the eluent to afford 3.10 g of olefin product A as a white solid (78% yield).

Synthesis of Aldehyde Intermediate B

A Schlenck flask was charged sequentially with A (1.00 g, 3.69 mmol), 4-bromobenzaldehyde (310 mg, 1.68 mmol), $Pd_2(dba)_3$ (15 mg), sodium carbonate (444 mg, 1.13 equiv.), and 2,6-di-t-butylcresol (732 mg, 0.33 mmol). The reaction mixture was then treated with dry dimethylacetamide (DMAC, 10 mL) and the flask flushed with $N_2$ for 20 min at room temperature. The reaction was then placed in an oil bath at 120° C. under $N_2$ for 24 hours. The color of the solution changed from light yellow to dark yellow. The reaction was stopped and $CH_2Cl_2$ (100 mL) was added, and washed with of DI water (2×100 mL). The organic layer was washed with saturated brine solution (100 mL), dried over anhydrous $Na_2SO_4$, and concentrated under reduced pressure. The crude product was then purified on silica gel using hexanes/$CH_2Cl_2$ (85:15) as the eluent to give the desired aldehyde product B as a yellow solid (600 mg, 45% yield).

Synthesis of WBI-PC-64

Combined B (404 mg, 1.076 mmol) was treated with cyanoacetic acid (92 mg, 1 equiv.) and piperidine (0.22 mL, 2 equiv.) in 30 mL of dry MeCN and flushed with $N_2$ at room temperature for 15 min. The reaction flask was then placed into an oil bath (82° C.) and refluxed under $N_2$ for 18 hours. The reaction turned from yellow to orange red and became homogeneous. The reaction was stopped, allowed to cool to room temperature and the solvent removed under reduced pressure. The residue was placed in a separatory funnel with 100 mL of $CH_2Cl_2$. The organic layer was washed with 0.1 N HCl solution (100 mL) and DI water (100 mL). The organic layer was then dried over anhydrous $Na_2SO_4$ and dried under reduced pressure to yield WBI-PC-64 (350 mg, 79% yield) as dark red crude product. LCMS (M+1): 443.1; 1H NMR (400 MHz, d6-DMSO): 8.29 (s, 1H), 8.10 (s, 2H), 7.75 (s, 2H), 7.32-6.92 (m, 16H).

Example 3

Synthesis of (E)-2-cyano-3-[4-[(E)-2-[4-(3,6-ditert-butylcarbazol-9-yl)phenyl]vinyl]-2,5-dimethoxy-phenyl]prop-2-enoic Acid (WBI-PC-66)

Synthetic Scheme:

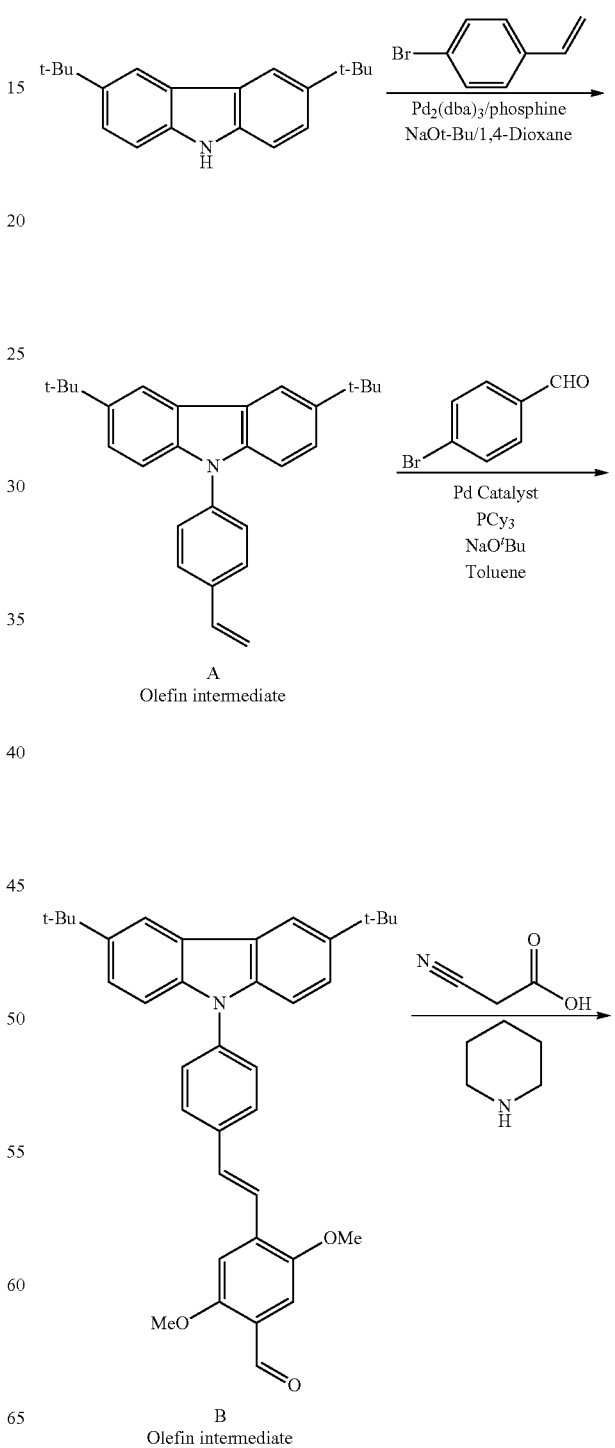

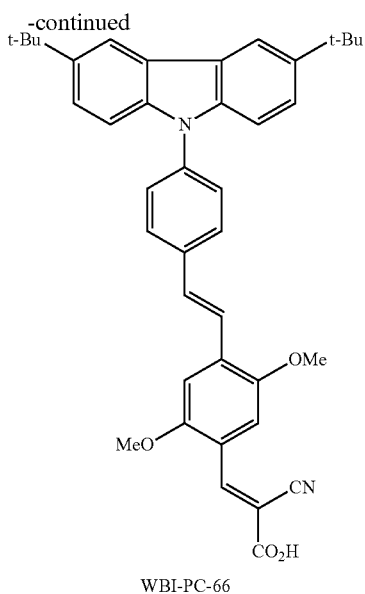

WBI-PC-66

Synthesis of Olefin Intermediate A

Bis(3,6-t-butyl)carbazole (0.0053 mol) and 4-bromostyrene (~0.7 mL, 10.0053 mol, equiv.) were combined in an oven dried 100 mL Schlenck flask with $Pd_2(dba)_3$ (48 mg, 0.0533 mmol), phosphine (36 mg, 1.06 mmol) and NaOtBu (0.56 g, 0.0059 mol). The flask was flushed with $N_2$ for 10 min, then dry, degassed 1,4-dioxane (10 mL) was added and the reaction was heated at 80° C. for 1.5 hours under $N_2$. The reaction was monitored by TLC to confirm consumption of starting materials and then cooled to room temperature. The organic layer was washed with DI water (2×25 mL), then saturated brine solution (25 mL). The organic layer was dried over anhydrous $Na_2SO_4$ and concentrated under reduced pressure. The resulting crude olefin intermediate A was used in the following step without further purification.

Synthesis of Aldehyde Intermediate B

The olefin intermediate A (5.0 mmol) was mixed with 4-bromo benzaldehyde (1.39 g, 5.0 mmol, 1.5 equiv.) in a 100 mL Schlenck vessel with dry toluene (30 mL) and flushed with $N_2$ for 20 min. To this solution were added Pd(dba)3 (92 mg, 2 mol %), tricyclohexylphosphine (57 mg, 4 mol %) and NaOtBu (724 mg, 1.5 equiv.) under $N_2$. The reaction mixture was then refluxed for 18 hours under $N_2$. The reaction was stopped and allowed to cool to room temperature. The mixture was treated with DI water (25 mL), the organic layer was then washed sequentially with 1N HCl (25 mL) and saturated brine (25 mL) solution. The organic layer was concentrated under reduced pressure and purified on silica gel column using Hexanes:DCM to give the aldehyde product B as a yellow solid (2.54 g, 78% yield).

Synthesis of WBI-PC-66

The aldehyde intermediate B (0.82 g, 2.70 mmol, oily solid) was placed in a RB flask with cyanoacetic acid (505 mg, 2.2 equiv.). Piperidine (1.23 mL, 4.6 equiv.) was added with 15 mL of dry MeCN. The mixture was placed under $N_2$ and stirred for 15 min. The mixture was then refluxed for 12 hours under $N_2$. The reaction was stopped and the MeCN was concentrated under reduced pressure to yield a residue. The residue was dissolved in 100 mL of EtOAC and washed with 50 mL of DI water. The organic layer was then washed with 0.1N HCl (75 mL). The organic layer was then analyzed by TLC and DART/MS (negative ion mode) and product formation was confirmed. The organic layer was concentrated under reduced pressure and the crude product was purified on silica gel using DCM:MeOH (100:0 to 90:10) to afford WBI-PC-66 as a yellowish red solid. 1H NMR (400 MHz, d6-DMSO) δ 8.54 (s, 1H), 8.29 (d, 2H), 7.89- (m, 10H), 5.75 (s, 2H), 3.98, 3.88 (2s, 3H), 1.41 (s, 18H).

Example 4

Synthesis of (Z)-2-cyano-3-[5-[4-(N-phenylanilino)phenyl]-2-furyl]prop-2-enoic Acid (WBI-PC-81)

Synthetic Scheme:

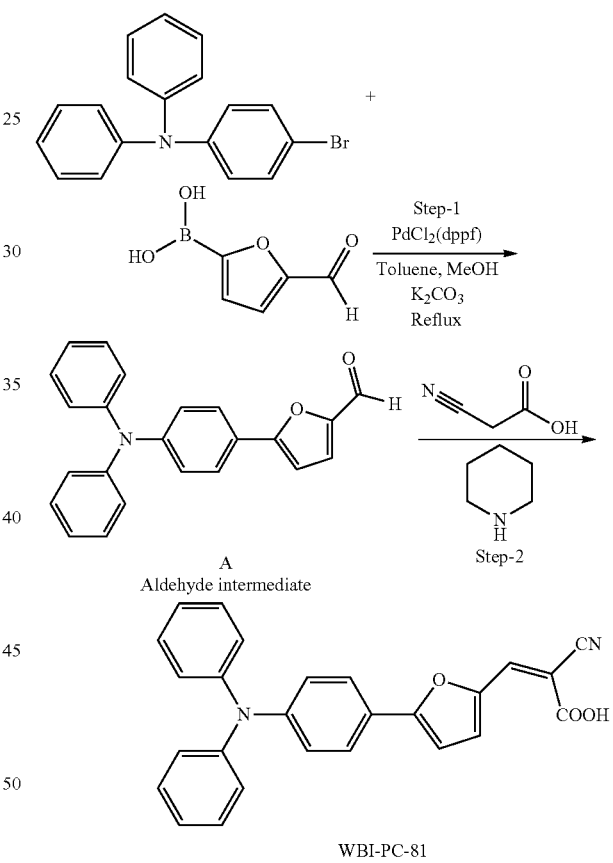

WBI-PC-81

Synthesis of Aldehyde Intermediate A

A mixture of 4-bromo-N,N-diphenyl-aniline (1.0 g, 3.08 mmol), $PdCl_2(dppf)$ (250 mg, 10 mol %), K2CO3 (2.12 g, 5 equiv.) were combined with 15 mL of dry toluene in a Schlenck tube and stirred under $N_2$ for 15 min at room temperature. The mixture was treated with (5-formyl-2-furyl)boronic acid (964 mg, 2 equiv.) in dry MeOH (5 mL), and the reaction was refluxed for 18 hours under $N_2$. The mixture was then cooled to room temperature and the solvents were removed under reduced pressure. The resulting residue was treated with DI water (20 mL) and extracted with DCM (50 mL). The organic layer was sequentially washed with DI water (20 mL), 1N HCl (25 mL) and saturated brine solution (25 mL). The organic layer was concentrated under reduced pressure and purified on silica gel using Hexanes: EtOAc as eluent to afford 5-[4-(N-phenylanilino)phenyl]furan-2-carbaldehyde (A) as a yellow red solid (900 mg, 82% yield).

Synthesis of WBI-PC-81

5-[4-(N-phenylanilino)phenyl]furan-2-carbaldehyde A (640 mg, 1.80 mmol) was combined with cyanoacetic acid (382 mg, 2.5 eq) and piperidine (0.931 mL, 2.1 eq with respect to cyanoacetic acid) in 10 mL of dry MeCN. The reaction was refluxed for 4 hours whereby the TLC indicated consumption of all starting material. The reaction was cooled down to room temperature and the MeCN was removed under reduced pressure. To the residue was added EtOAc (50 mL), washed with DI water (50 mL) followed by 0.1 N HCl (50 mL). The organic layer was separated, concentrated and then the crude mixture was then purified using a silica gel column using DCM: MEOH as eluent to afford WBI-PC-81 as a dark red solid (600 mg, 79% yield). LCMS (M+1): 407.1; 1HNMR (400 MHz, d6-DMSO) 7.99 (s, 1H), 7.77 (s, 2H), 7.60 (s, 1H), 7.40 (m, 4H), 7.22-7.08 (m, 7H), 6.94 (s, 2H).

Example 5

Synthesis of 7-[(E)-2-[4-(4-tert-butyl-N-(4-tert-butylphenyl)anilino)phenyl]vinyl]-2-oxo-1H-quinoline-3-carbonitrile (WBI-PC-174)

Synthetic Scheme:

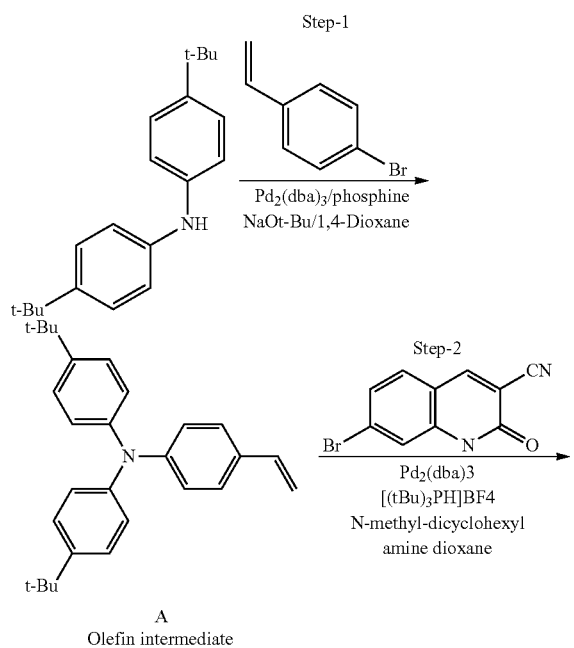

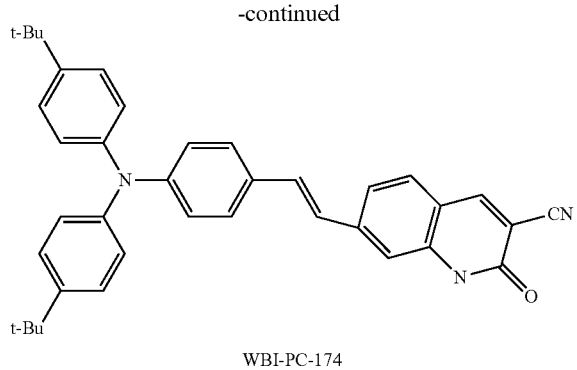

Synthesis of Olefin Intermediate A

To a mixture of Bis((4-t-butyl)phenyl)amine (15.0 g, 0.053 mol) and 4-bromostyrene (~7 mL, 1 equiv.) in an oven dried 500 mL Schlenck flask was added Pd$_2$(dba)$_3$ (488 mg, 0.533 mmol), phosphine (360 mg, 1.06 mmol) and NaOtBu (5.63 g, 0.059 mol). The flask was flushed with N$_2$ for 10 min and treated with degassed 1,4-dioxane (50 mL) was added, and the mixture was heated at 80° C. for 1.5 hours under N$_2$. The reaction was monitored by TLC for completion before cooling to room temperature. The organic layer was washed with DI water (2×100 mL) and then saturated brine solution (100 mL). The organic layer was then dried over anhydrous Na$_2$SO$_4$ and concentrated under reduced pressure. The resulting crude olefin product was used in the following step without further purification.

Synthesis of WBI-PC-174

1.0 equiv. of 7-bromo-2-oxo-1H-quinoline-3-carbonitrile, 0.025 equiv. Pd$_2$(dba)$_3$ and 0.05 equiv. tBu3PHBF4 were added to 1.0 equiv. of N,N-bis(4-tert-butylphenyl)-4-vinyl-aniline in a round bottom flask. The flask was purged with N$_2$ for 20 min. Dry dioxane was degassed by bubbling with N$_2$ for 20 minutes. Dioxane was added to the reaction (0.2 M) followed by 1.5 equiv. N-methyl-di-cyclohexyamine. The solution was heated to 65° C. and monitored by LCMS, TLC 30% ethyl acetate/hexane. After 1.5 hours the reaction had solidified. 4.0 mL of N$_2$ degassed dry dioxane were added to redissolve the material and the styrene was consumed within 2.5 hours as indicated by TLC. The reaction mixture, a solid mass, was cooled to room temperature, residual solvent was removed under reduced pressure. The crude reaction product was partitioned between 50 mL of CH$_2$Cl$_2$ and 20 mL of 1M HCl and the insoluble material was filtered off. The layers were separated, and the aqueous layer was back extracted 2×25 mL of CH$_2$Cl$_2$. The combined organic layer was dried over Na$_2$SO$_4$, filtered and concentrated under reduced pressure to afford WBI-PC-174. 1HNMR (400 MHz, d6-DMSO) 8.10 (s, 1H), 7.60-6.91 (m, 17H), 1.26 (s, 18H).

General Synthetic Scheme for Making Compounds with Acid Linkers
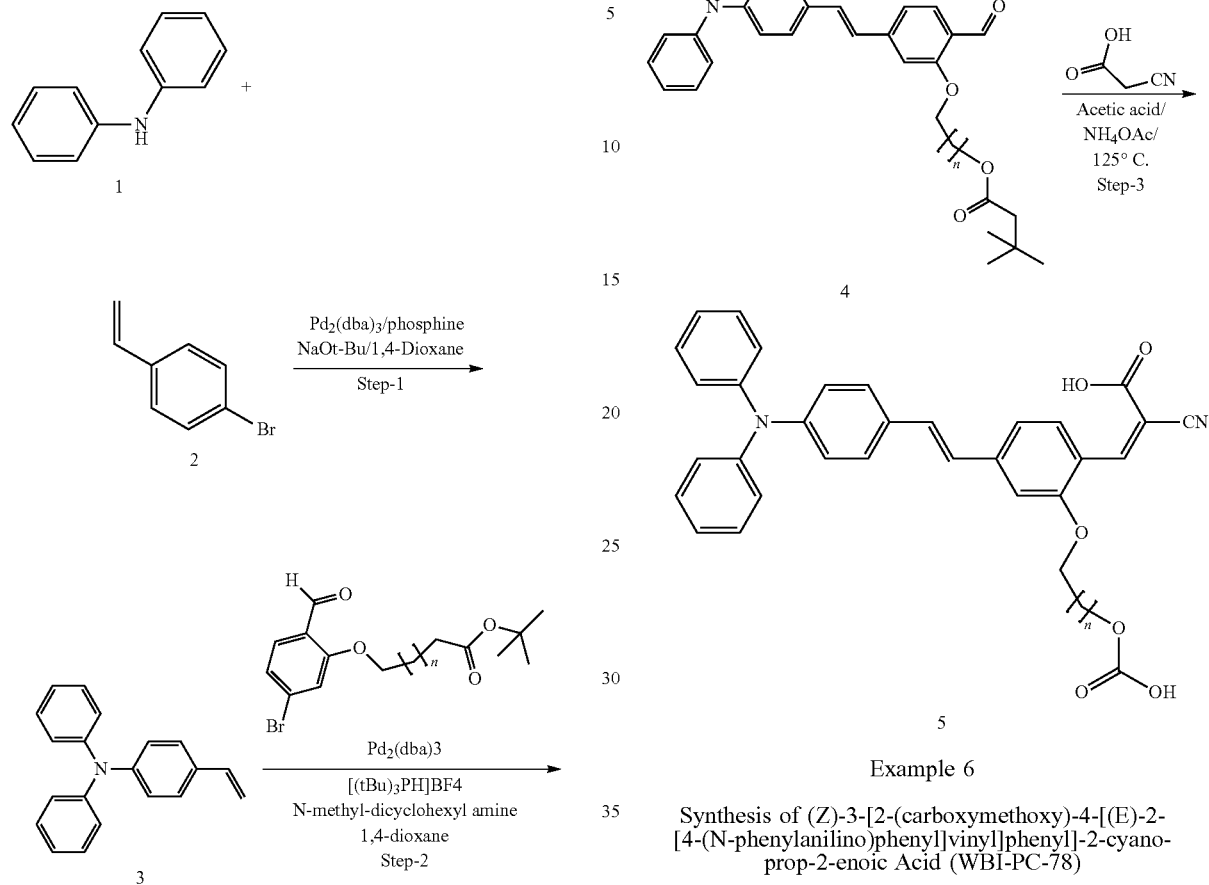
Example 6
Synthesis of (Z)-3-[2-(carboxymethoxy)-4-[(E)-2-[4-(N-phenylanilino)phenyl]vinyl]phenyl]-2-cyano-prop-2-enoic Acid (WBI-PC-78)
Synthetic Scheme:
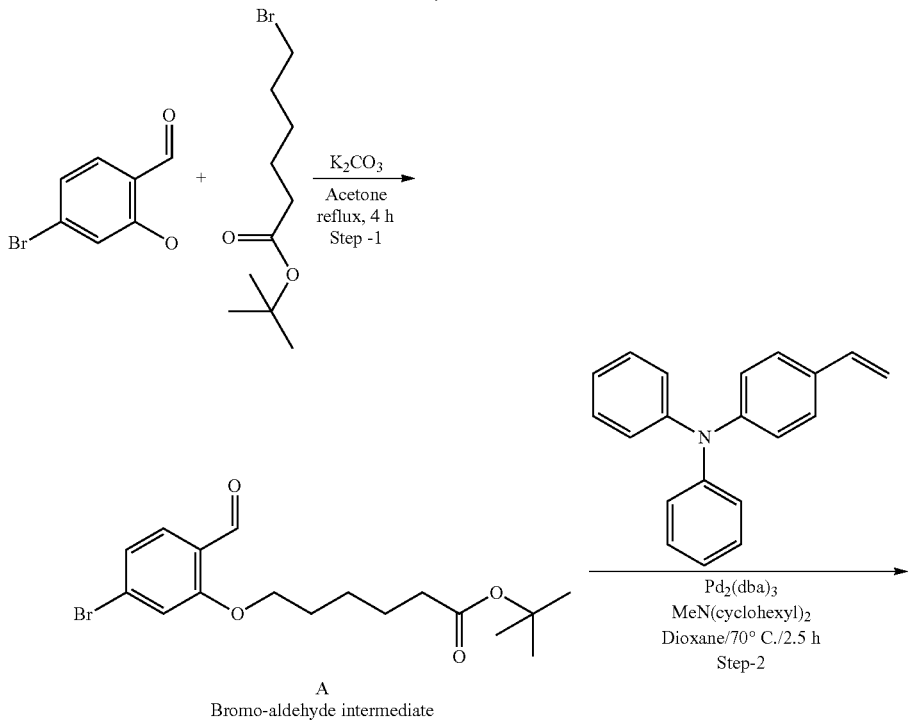
A
Bromo-aldehyde intermediate

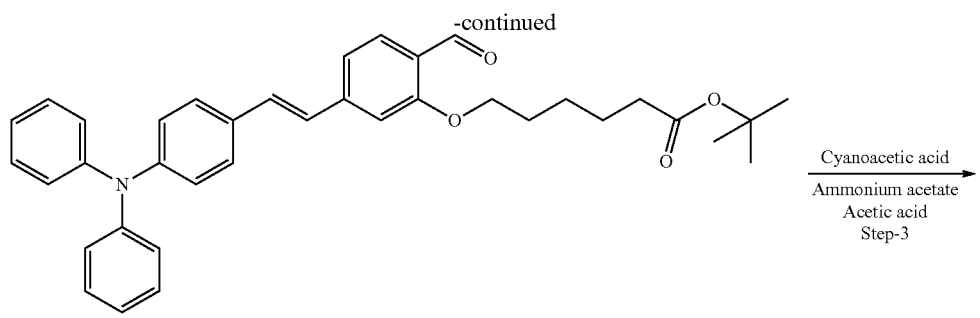

B
Aldehyde intermediate with acid linker

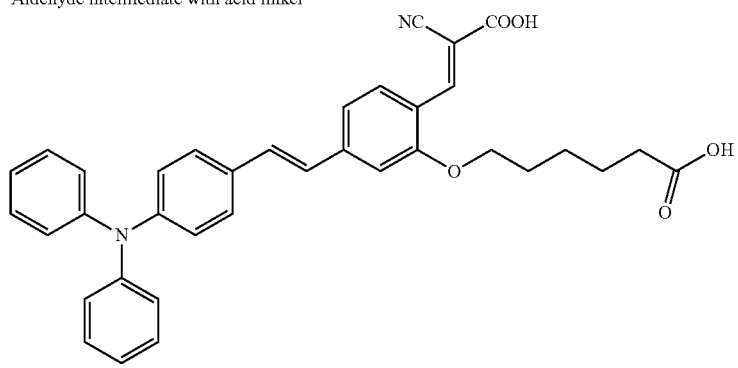

WBI-PC-190

Synthesis of the Bromoaldehyde Intermediate with Acid Linker (A)

A mixture of 4-bromo-2-hydroxybenzaldehyde (1.5 g, 7.4 mmol), tert-butyl 6-bromohexanoate (9.0 mmol) and potassium carbonate (3.2 g, 22.5 mmol) were taken in acetone (10 mL). The reaction mixture was refluxed for 4 h. The reaction mixture was extracted with ethyl acetate (2×25 mL), dried over anhydrous $Na_2SO_4$ and concentrated under reduced pressure. Purification on silica gel afforded 1.1 g of the desired compound A as a white solid.

Synthesis of the Aldehyde Intermediate with Acid Linker (B)

To the N,N-diphenyl-4-vinyl-aniline (0.003 mol) in a two necked flask under $N_2$ was added the bromo-aldehyde intermediate A (0.004 mol) and N-methyl-dicylohexyl amine (0.008 mol). $Pd_2(dba)_3$ (0.04 g, 0.044 mmol) and phosphine salt (0.022 g, 0.007 mmol) were then added to the flask under $N_2$. Dry and degassed 1,4-dioxane (10 mL) was added to the flask. The mixture was stirred at 70° C. under $N_2$ for 2.5 hours. The reaction mixture was extracted with ethyl acetate, dried over anhydrous $Na_2SO_4$ and concentrated under reduced pressure. Purification on silica gel afforded 1.4 g of the desired compound B.

Synthesis of WBI-PC-78

In a 20 mL microwave tube, the intermediate B (3 mmol), 2-cyanoacetic acid (5.1 mmol) and ammonium acetate (8 mmol) were mixed in acetic acid (15 mL). The reaction mixture was heated at 130° C. for 90 min. Water (10 mL) was added, and the solid was filtered, and dried under reduced pressure to give the product WBI-PC-78. LCMS (M+1): 559.7; 1H NMR (400 MHz, d6-DMSO) 8.54 (s, 1H), 8.17 (s, 1H), 7.32-7.30 (m, 9H), 7.06-7.03 (m, 9H), 4.19 (t, 2H), 2.47 (t, 2H), 1.88-1.66 (m, 4H).

Example 7

Synthesis of (Z)-3-[2-(carboxymethoxy)-4-[(E)-2-[4-(N-phenylanilino)phenyl]vinyl]phenyl]-2-cyano-prop-2-enoic Acid WBI-PC-190

Synthetic Scheme:

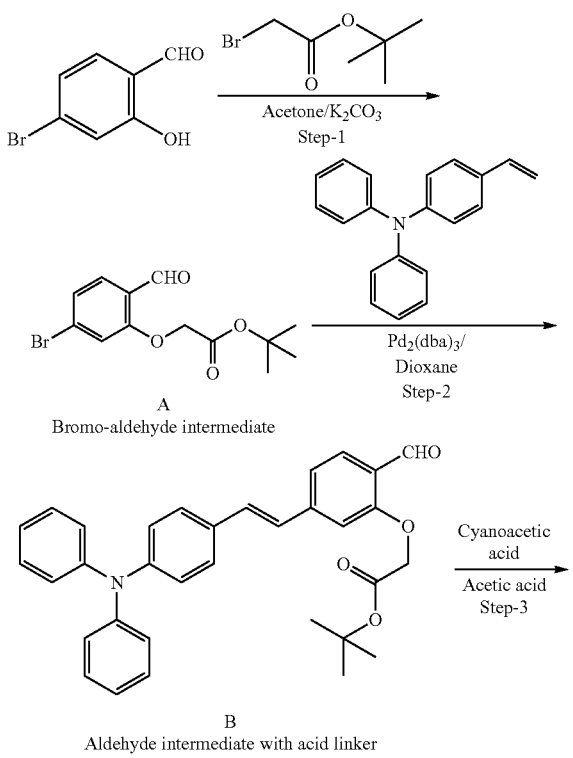

B
Aldehyde intermediate with acid linker

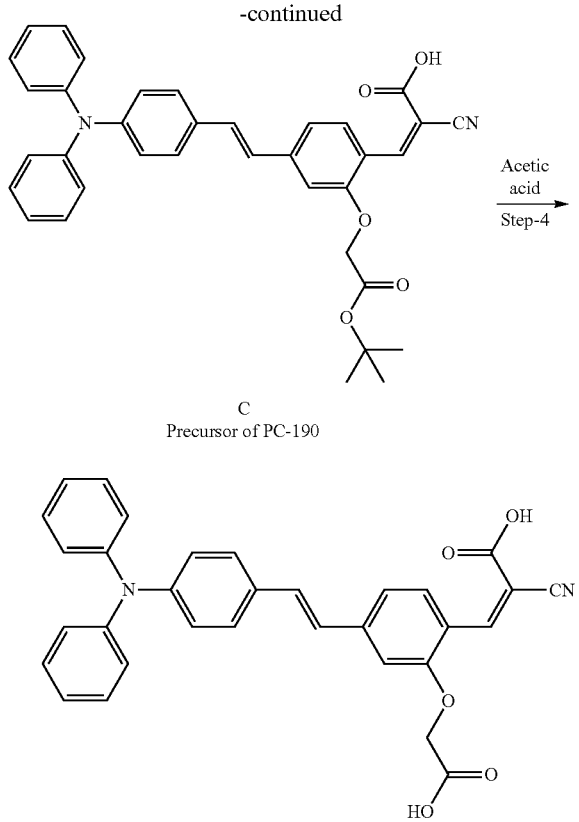

C
Precursor of PC-190

WBI-PC-190

Synthesis of the Bromoaldehyde Intermediate with Acid Linker

In a 250 mL round bottom flask, 4-bromo-2-hydroxybenzaldehyde (3 g, 14.9 mmol), tert-Butyl bromoacetate (3.49 g, 17.9 mmol) and potassium carbonate (6.19 g, 44.8 mmol) were dissolved in acetone (30 mL). The reaction mixture was refluxed for 4 hours. The reaction mixture was then extracted with ethyl acetate (2×25 mL), dried over anhydrous $Na_2SO_4$ and concentrated under reduced pressure. Purification on silica gel afforded 2.8 g (59% yield) of the desired compound A as white solid. 1H NMR (400 MHz, CDC 3): 10.46 (s, 1H), 7.71 (d, 1H), 7.24 (s, 1H), 6.99 (s, 1H), 4.61 (s, 2H), 1.47 (s, 9H).

Synthesis of the Aldehyde Intermediate with Acid Linker

To the N,N-diphenyl-4-vinyl-aniline (2 g, 0.007 mol) in a two necked flask under $N_2$ was added 4-bromo-2,5-dimethoxy benzaldehyde (2.44 g, 0.008 mol) and N-methyl-dicyclohexyl amine (3.3 mL, 0.016 mol). $Pd_2(dba)_3$ (0.081 g, 0.088 mmol) and phosphine salt (0.043 g, 0.0014 mmol) were then added to the flask under $N_2$. Dry and degassed 1,4-dioxane (10 mL) was added to the flask. The mixture was stirred at 70° C. under $N_2$ for 2.5 hours. The mixture turned from purple to yellow green upon stirring. TLC analysis (Hex:Ethyl acetate 10:1) after 2.5 hours showed complete consumption of 4-bromo-2,5-dimethoxy benzaldehyde and the formation of the desired product (confirmed by LCMS). The reaction mixture was extracted with ethyl acetate, dried over anhydrous $Na_2SO_4$ and evaporated. Purification by combiflash afforded 2.2 g of desired compound B. LCMS (M+1): 505.9; 1H NMR (400 MHz, $CDCl_3$): 10.48 (s, 1H), 7.80 (d, 1H), 7.40-7.04 (m, 19H), 6.99 (s, 1H), 4.67 (s, 2H), 1.47 (s, 9H).

Synthesis of WBI-PC-190

In a 20 mL microwave tube, tert-butyl 2-[2-formyl-5-[(E)-2-[4-(N phenylanilino)phenyl]vinyl]-phenoxy]-acetate (1.3 g, 3 mmol), 2-cyanoacetic acid (0.46 g, 5.1 mmol) and ammonium acetate (0.595 g, 8 mmol) were mixed in 15 mL of acetic acid. The reaction mixture was heated at 130° C. for 20 min. LCMS showed desired mass peak along with tertiary group deprotected product. Water (10 mL) was added, and the solid was filtered, and dried under reduced pressure to give the product WBI-PC-190 (0.6 g, 83% yield) red solid. LCMS (M+1): 516.6; 1H NMR (400 MHz, d6-DMSO): 8.60 (s, 1H), 8.18 (s, 1H), 7.34-6.98 (m, 20H), 4.92 (s, 2H).

Example 8

Synthesis of WBI-PC-191

Synthesis of tert-Butyl-8-bromooctanoic Acid Intermediate

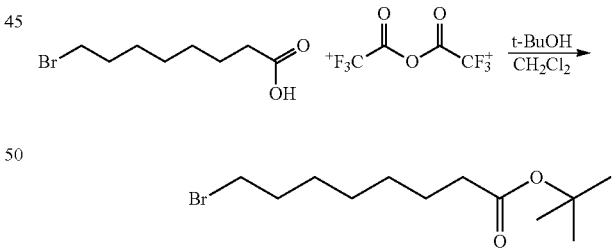

To a solution of 8-bromooctanoic acid (5 g, 22 mmol) in DCM (20 mL) was added TFAA (10.36 g, 49 mmol) dropwise at 0° C. After 2.5 hours, t-BuOH (5.81 g, 70 mmol) was slowly added. After 1 hour, the reaction had warmed to rt. After 2.5 hours, the reaction was quenched with H2O (10 mL) and extracted with ethyl acetate (2×20 mL). The combined organic layer was washed with brine and dried over $MgSO_4$, filtered, and concentrated under reduced pressure. The crude (6.89 g) was used in the next step without further purification.

Synthesis of the Aldehyde Intermediate by O-alkylation of 4-bromo-2-hydroxy-benzaldehyde with Tert-Butyl Ester Linker

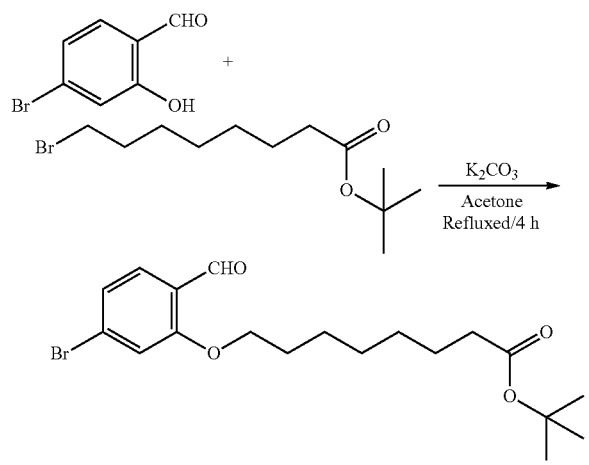

In a single necked round bottom flask, 4-bromo-2-hydroxy-benzaldehyde (3 g, 0.015 mol), tert-butyl 8-bromooctanoate (4.16 g, 0.015 mol) and K2CO3 (4.12 g, 0.03 mol) were dissolved in dry DMF (30 mL). The reaction mixture was heated at 70° C. for 16 hours. LCMS showed the desired mass peak. The crude reaction mixture was extracted with ethyl acetate, washed with water, dried over anhydrous $Na_2SO_4$ and concentrated under reduced pressure. Purification on silica gel using Hexane/Ethyl acetate (97:3) afforded 2.4 g (40% yield) of desired product. 1H NMR (400 MHz, CDCl3): 10.39 (s, 1H), 7.67 (d, 1H), 7.11 (d, 2H), 4.03 (t, 2H), 2.21 (t, 2H), 1.80-1.23 (m, 10H), 1.41 (s, 9H).

Synthesis of the Triphenylamine Styryl Aldehyde Intermediate Tert-Butyl Ester Linker Product To the N,N-diphenyl-4-vinyl-aniline (2 g, 0.007 mol) in a two necked flask under $N_2$ was added tert-butyl 8-(5-bromo-2-formyl-phenoxy)octanoate (3.09 g, 0.008 mol) and N-methyl-dicylohexyl amine (3.05 g, 0.0.016 mol). $Pd_2$(dba)$_3$ (0.081 g, 0.088 mmol) and phosphine salt (0.043 g, 0.0014 mmol) were then added to the flask under $N_2$. Dry and degassed 1,4-dioxane (10 mL) was added to the flask. The mixture was stirred at 70° C. under $N_2$ for 2.5 hours. The mixture turned from purple to yellow green upon stirring. TLC analysis (Hexane:Ethyl acetate 10:1) after 2.5 hours showed complete consumption of tert-butyl 8-(5-bromo-2-formyl-phenoxy)octanoate and the formation of the desired product (confirmed by LCMS). Purification on silica gel afforded 2.3 g (50% yield) of the desired product. 1H NMR (400 MHz, CDCl$_3$): 10.40 (s, 1H), 7.66 (d, 1H), 7.13 (d, 2H), 4.04 (t, 2H), 2.19 (t, 2H), 1.81-1.28 (m, 14H), 1.41 (s, 9H).

Synthesis of the Cyanoacrylic Acid Intermediate by Knoevenagel Condensation

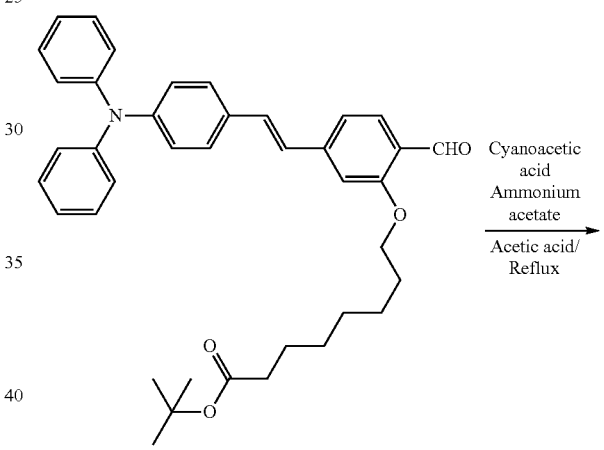

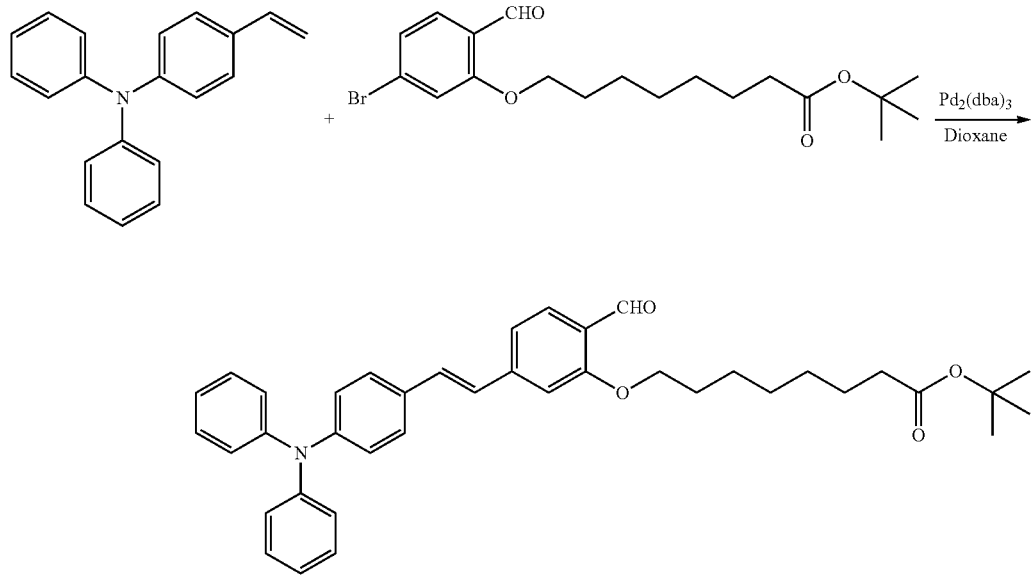 [SMILES: C=Cc1ccc(N(c2ccccc2)c2ccccc2)cc1 ; CC(C)(C)OC(=O)CCCCCCCOc1cc(Br)ccc1C=O ; CC(C)(C)OC(=O)CCCCCCCOc1cc(/C=C/c2ccc(N(c3ccccc3)c3ccccc3)cc2)ccc1C=O]

-continued

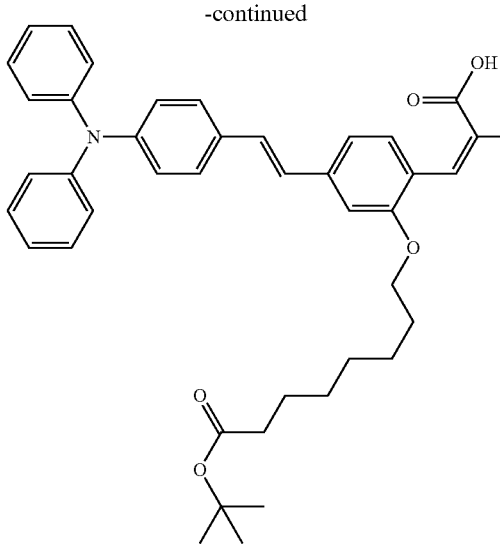

In a 20 mL microwave tube, tert-butyl 8-[2-formyl-5-[(E)-2-[4-(N-phenylanilino)phenyl]vinyl]phenoxy]octanoate (1.5 g, 3 mmol), 2-cyanoacetic acid (0.454 g, 5 mmol) and ammonium acetate (0.588 g, 8 mmol) were dissolved in 15 mL of acetic acid. The reaction mixture was heated at 130° C. for 20 min. LCMS showed the desired mass peak along with tertiary group deprotected product. Water (10 mL) was added and filtered. The collected solid was used in the next step without further purification.

Synthesis of WBI-PC-191 by Tert-Butyl Deprotection

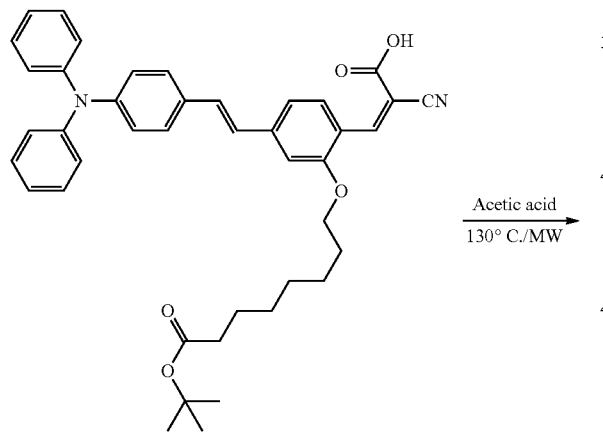

-continued

In a 20 mL microwave tube, (Z)-3-[2-(8-tert-butoxy-8-oxo-octoxy)-4-[(E)-2-[4-(N-phenylanilino)phenyl]vinyl]phenyl]-2-cyano-prop-2-enoic acid (1 g, 1.52 mmol) was dissolved in 10 mL acetic acid and 1 mL water. The reaction mixture was heated at 130° C. for 20 min. The reaction was repeated two times for 20 min each in the microwave. LCMS showed the desired mass peak. Water (10 mL) was added and filtered. The collected solid was dried under reduced pressure to give WBI-PC-191 0.650 g (61% yield) as a red solid. LCMS (M+1): 600.7; 1H NMR (400 MHz, d6-DMSO): 8.56 (s, 1H), 8.18 (s, 1H), 7.60-6.91 (m, 20H), 4.16 (br s, 2H), 2.18 (br s, 2H), 1.89 (br s, 2H), 1.58-1.20 (m, 8H).

Example 9

Synthesis of WBI-PC-192

Synthesis of the tert-Butyl-10-bromodecanoic Acid Intermediate

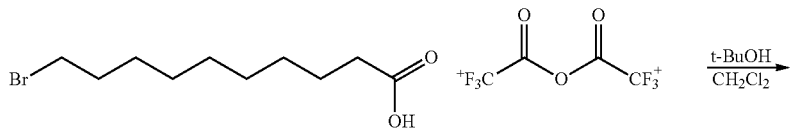

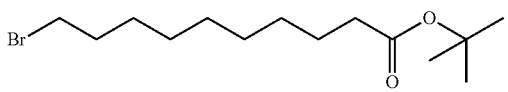

To solution of 10-bromdectanoic acid (5 g, 20 mmol) in DCM (20 mL) was added TFAA (9.2 g, 44 mmol) dropwise at 0° C. After 2.5 hours, t-BuOH (5.16 g, 70 mmol) was slowly added. After 1 hour the reaction had warmed to RT. After 2.5 hours, the reaction was quenched with H2O (5 mL) and extracted with ethyl acetate (2×20 mL). The combined organic layer was washed with brine and dried over MgSO₄, filtered, and concentrated under reduced pressure. The crude (6.12 g) was used in the next step without further purification.

Synthesis of the Aldehyde Intermediate by O-alkylation of 4-bromo-2-hydroxy-benzaldehyde with Tert-Butyl Ester Linker

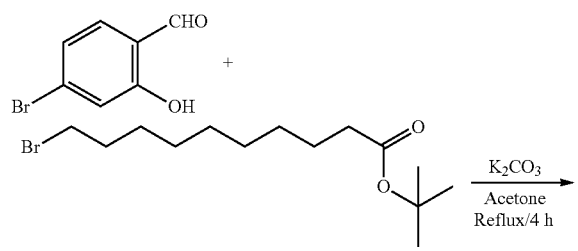

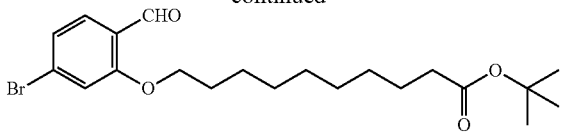

In a single necked round bottom flask, 4-bromo-2-hydroxy-benzaldehyde (3 g, 0.015 mol), tert-butyl 10-bromo-decanoate (5.04 g, 0.016 mol) and K2CO3 (6.18 g, 0.045 mol) were dissolved in dry DMF (30 mL). The reaction mixture was heated at 70° C. for 16 hours. LCMS showed the desired mass peak. The crude reaction mixture was extracted with ethyl acetate, washed with water, dried over anhydrous Na₂SO₄ and concentrated under reduced pressure. Purification on silica gel afforded 3.2 g (50% yield) of the desired product.

Synthesis of the Triphenylamine Styryl Aldehyde Intermediate Tert-Butyl Ester Linker

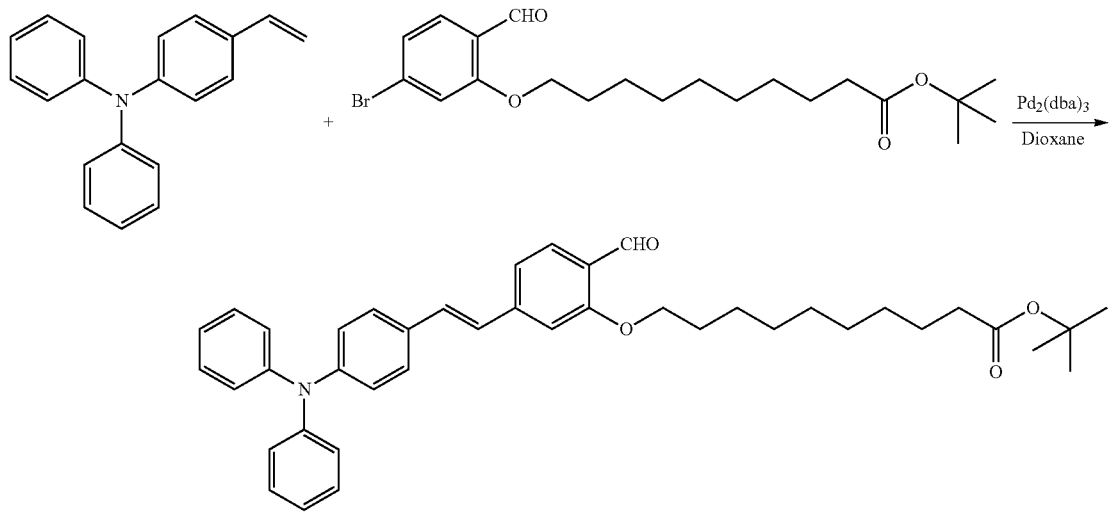

To the N,N-diphenyl-4-vinyl-aniline (2 g, 7.74 mmol) in a two necked flask under N₂ was added tert-butyl 10-(5-bromo-2-formyl-phenoxy)decanoate (3.307 g, 7.75 mmol) and N-methyl-dicylohexyl amine (3.05 g, 15.56 mmol). Pd₂(dba)₃ (0.081 g, 0.8 mmol) and tri-tert-butylphosphonium tetrafluoroborate (0.043 g, 1.4 mmol) were then added to the flask under N₂. Dry and degassed 1,4-dioxane (10 mL) was added to the flask. The mixture was stirred at 70° C. under N₂ for 2.5 hours. The mixture turned from purple to yellow green upon stirring. TLC analysis (Hexane:Ethyl acetate 10:1) after 2.5 hours showed complete consumption of tert-butyl 10-(5-bromo-2-formyl-phenoxy)decanoate and the formation of the desired product (confirmed by LCMS). Purification on silica gel afforded 2.3 g of desired product as a yellow liquid. 1H NMR (400 MHz, d6-DMSO): 10.43 (s, 1H), 7.82 (s, 1H), 7.41-6.98 (m, 16H), 4.10 (t, 2H), 2.20 (t, 2H), 1.90-1.209 (m, 14H), 1.42 (s, 9H).

Synthesis of the Cyanoacrylic Acid Intermediate by Knoevenagel Condensation

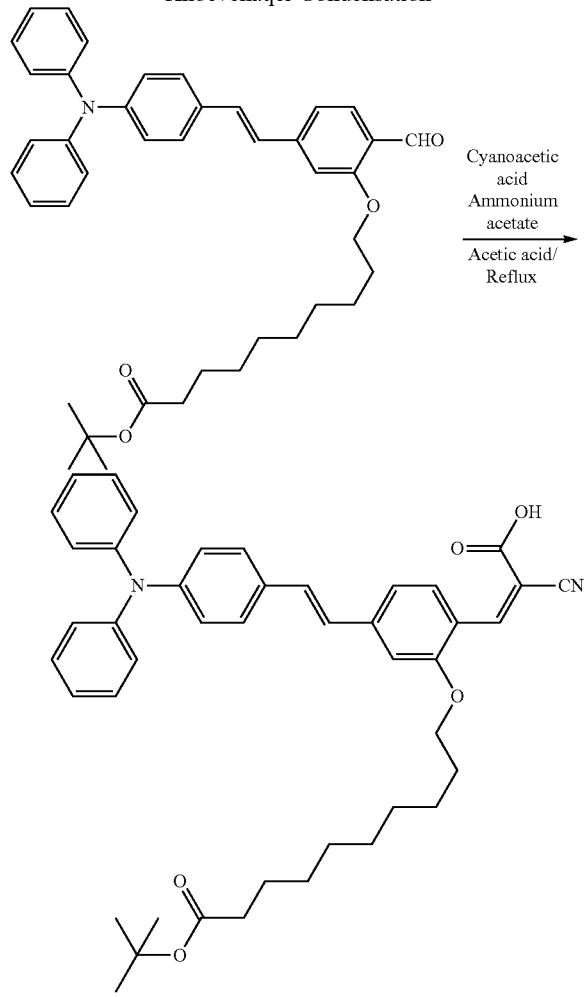

In a 20 mL microwave tube, tert-butyl 10-[2-formyl-5-[(E)-2-[4-(N-phenylanilino)phenyl]vinyl]phenoxy]-decanoate (1.5 g, 2.43 mmol), 2-cyanoacetic acid (0.434 g, 5.1 mmol) and ammonium acetate (0.561 g, 7.23 mmol) were dissolved in 15 mL acetic acid. The reaction mixture was heated at 130° C. for 20 min. LCMS showed the desired mass peak along with the tertiary group deprotected product. Water (10 mL) was added and filtered. The collected solid was used in the next step without further purification.

Synthesis of WBI-PC-192 by Tert-Butyl Deprotection

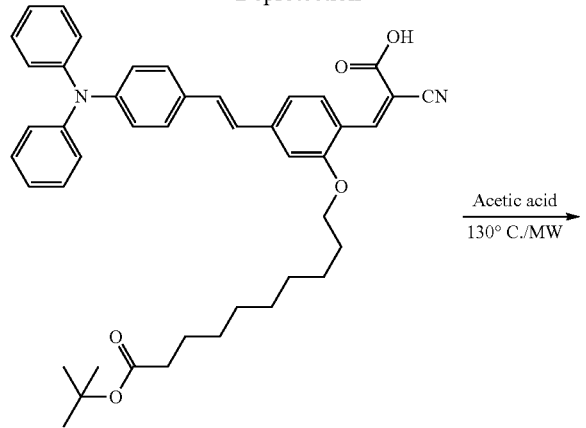

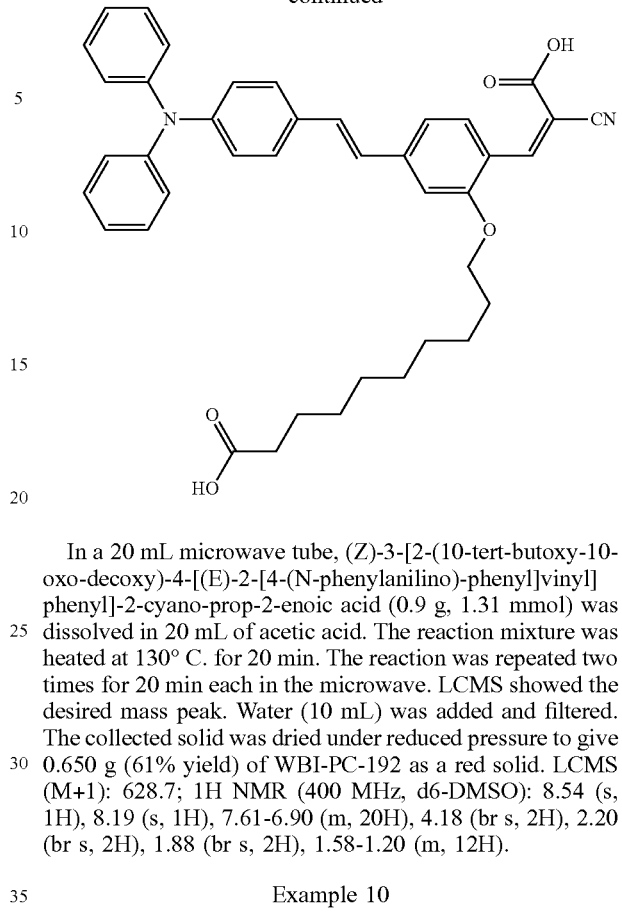

In a 20 mL microwave tube, (Z)-3-[2-(10-tert-butoxy-10-oxo-decoxy)-4-[(E)-2-[4-(N-phenylanilino)-phenyl]vinyl]phenyl]-2-cyano-prop-2-enoic acid (0.9 g, 1.31 mmol) was dissolved in 20 mL of acetic acid. The reaction mixture was heated at 130° C. for 20 min. The reaction was repeated two times for 20 min each in the microwave. LCMS showed the desired mass peak. Water (10 mL) was added and filtered. The collected solid was dried under reduced pressure to give 0.650 g (61% yield) of WBI-PC-192 as a red solid. LCMS (M+1): 628.7; 1H NMR (400 MHz, d6-DMSO): 8.54 (s, 1H), 8.19 (s, 1H), 7.61-6.90 (m, 20H), 4.18 (br s, 2H), 2.20 (br s, 2H), 1.88 (br s, 2H), 1.58-1.20 (m, 12H).

Example 10

Biological Testing

Materials

Human peptides Aβ1-42 and Amylin 8-37 were purchased from China Peptide and stored at −80° C. Zinc sulfate heptahydrate ($ZnSO_4 \cdot 7H_2O$), BisANS (4,4'-Dianilino-1,1'-binaphthyl-5,5'-disulfonic acid dipotassium salt), Epigallocatechin-3-gallate (EGCG), 9-(Dicyanovinyl)julolidine (DCVJ) and Clioquinol (CQ) were purchased from Sigma Aldrich. Ethylenediaminetetraacetic acid (EDTA) was purchased from Alfa Aesar. 2-(dimethylamino)methyl-5,7-dichloro-8-hydroxyquinoline (AC-068), structurally similar to PBT-2 was synthesized by Warner Babcock Institute for Green Chemistry, LLC.

Fluorescence-Based Assays of Aβ Disaggregation

As disaggregation was assessed using a Spectramax M5 multi-mode microplate reader (Molecular Devices) using untreated black 96-well plates (Costar #3915). The device was configured to maintain 26° C., measure an excitation of 390 nm, emission of 490 nm and cutoff 475 nm with the PMT+set at Medium, 6 flashes/read at 40 second intervals with shaking 5 seconds before the first read and 3 seconds between reads.

Experiments were conducted at 26° C. in a Tris-HCl buffer (50 mM, pH7.4) containing NaCl (150 mM). Aβ1-42 was solubilized in DMSO to a concentration of 1.5 mM for 5 minutes then briefly centrifuged to remove any aggregates. The soluble Aβ1-42 (15 μM) was immediately mixed ±bis-ANS (15 μM) and allowed to equilibrate for 5 minutes. Aβ aggregation was induced with the addition of ±Zn (15 μM) in H2O. The fluorescence response was measured until a plateau was reached at approximately 45 minutes. Test compounds (0.227-60 μM in DMSO) were then added and the dose response was measured over a 20-minute period. EDTA, known to chelate Zn, was used as a positive control. Raw fluorescence was normalized to background fluorescence without Aβ and expressed as a percentage of that in control samples without Zn. All quantitative data was expressed as mean±SEM from at least 3 replicates. All statistical analysis was conducted with Prism 6 (GraphPad). Nonlinear regression was used to calculate the concentration at which fluorescence was reduced by 50 percent ($EC_{50}$), as shown in Table 1.

TABLE 1

$EC_{50}$ values of Aβ1-42:Zn disaggregation by select compounds

| Compound | $EC_{50}$ (Avg) | StDev |
|---|---|---|
| PC-063 | 31.041 | 16.945 |
| PC-064 | 0.747 | 0.090 |
| PC-078 | 1.376 | 0.110 |
| PC-081 | 0.338 | 0.031 |
| PC-174 | 49.650 | 238.498 |
| PC-190 | 0.649 | 0.072 |
| PC-191 | 1.613 | 0.281 |
| PC-192 | 2.848 | 0.550 |
| CQ | 2.693 | 0.196 |
| DCVJ | 0.533 | 0.188 |
| EDTA | 46.120 | 38.551 |
| AC-068(PBT2) | 2.215 | 0.271 |

Fluorescence-Based Assays of Amylin Disaggregation

Amylin disaggregation was assessed using a Spectramax M5 multi-mode microplate reader (Molecular Devices) using untreated black with clear bottom 96 well plates (Costar #3631). The device was configured to maintain 26° C., measure an excitation of 390 nm, emission of 490 nm and cutoff 475 nm with the PMT+set at Medium, 6 flashes/read at 5-minute intervals with shaking 5 seconds before the first read and 3 seconds between reads.

Experiments were conducted at 26° C. in a Tris-HCl buffer (50 mM, pH7.4) containing NaCl (150 mM). Amylin 8-37 peptide was solubilized in DMSO to a concentration of 1.5 mM for 5 minutes then briefly centrifuged to remove any aggregates. The soluble amylin peptide (15 μM) was immediately mixed ±bis-ANS (15 μM) and the plate sealed to prevent evaporation. Aggregation was measured by an increase in fluorescence over 24 hours. Test compounds (0.227-60 μM in DMSO) were then added and the dose response was measured over a 24 hour period. EGCG was used as a positive control. Raw fluorescence was normalized to background fluorescence without Amylin and expressed as a percentage of that in control samples. All quantitative data was expressed as mean±SEM from at least 3 replicates. All statistical analysis was conducted with Prism 6 (Graph-Pad). Nonlinear regression was used to calculate the concentration at which fluorescence was reduced by 50 percent ($EC_{50}$), as shown in Table 2.

TABLE 2

$EC_{50}$ values of Amylin Disaggregation by select compounds

| Compound | $EC_{50}$ | StDev |
|---|---|---|
| PC-063 | 1.259 | 0.693 |
| PC-064 | 0.024 | 0.043 |
| PC-066 | 1.191 | 0.309 |
| PC-081 | 0.207 | 0.111 |
| PC-174 | 3.740 | 6.464 |

TABLE 2-continued $EC_{50}$ values of Amylin Disaggregation by select compounds

| Compound | $EC_{50}$ | StDev |
|---|---|---|
| CQ | 4.074 | 3.036 |
| EGCG | 0.857 | 0.491 |

What is claimed is:

1. A compound of formula I:

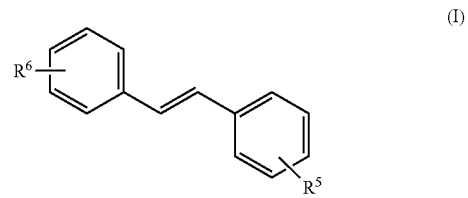

(I)

wherein
$R^6$ is —$NR^3R^4$;
$R^5$ is —$(CR=CR-)_n(CR=CR^2-)R^1$;
n is an integer from 0 to 10;
$R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H;
each R is independently selected from —H and $C_{1-6}$ linear or branched alkyl; and
$R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, provided that
if n=0, and $R^3$ and $R^4$ are both: (a) H; (b) substituted or unsubstituted linear or branched $C_1$-$C_{10}$ alkyl; or (c) substituted or unsubstituted phenyl or $C_6$-$C_{10}$ aryl, then $R^1$ and $R^2$ are not both selected from the group consisting of —H, —CN, —COOR, —$PO_3HR$, and —CONHR.

2. The compound of claim 1 having the formula II:

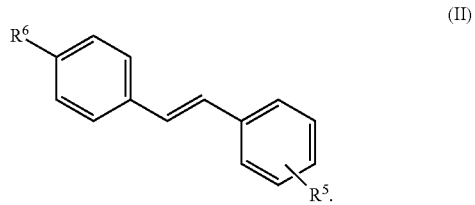

(II)

3. The compound of claim 1 having the formula III:

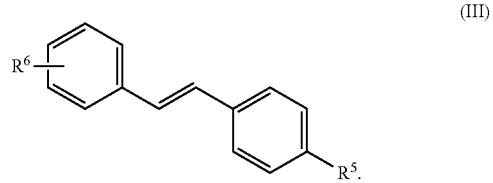

(III)

4. The compound of claim 1 having the formula IV:

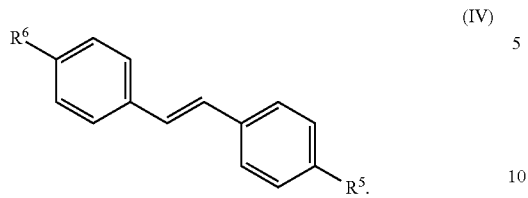

(IV)

5. The compound of claim 1 wherein $R^6$ is selected from the group consisting of diethylamino, diphenylamino, methyl(phenyl)amino, cyclohexyl(methyl)amino, bis(4-methoxyphenyl)amino, bis(4-(tert-butyl)phenyl)amino, di(pyridin-2-yl)amino, di(pyridin-3-yl)amino, di(pyridin-4-yl)amino, piperidin-1-yl, 4-methylpiperazin-1-yl, 4-phenylpiperazin-1-yl, pyrrolidin-1-yl, and morpholino.

6. The compound of claim 1 wherein $R^3$ and $R^4$ are substituted or unsubstituted phenyl.

7. The compound of claim 4 wherein $R^1$ and $R^2$ together are —CN and —COOH.

8. A pharmaceutical composition comprising a therapeutically effective amount of a compound of claim 1 and a pharmaceutically acceptable excipient.

* * * * *